US005610121A

United States Patent [19]

Riebel et al.

[11] Patent Number: 5,610,121

[45] Date of Patent: Mar. 11, 1997

[54] HETEROCYCLICALLY DISUBSTITUTED SULPHONYLAMINO(THIO)CARBONYL COMPOUNDS

[75] Inventors: Hans-Jochem Riebel, Wuppertal; Ernst R. F. Gesing, Erkrath-Hochdahl; Klaus-Helmut Müller, Düsseldorf; Peter Müller, Langenfeld; Kurt Findeisen; Hans-Joachim Santel, both of Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 335,797

[22] PCT Filed: May 17, 1993

[86] PCT No.: PCT/EP93/01227

§ 371 Date: Nov. 15, 1994

§ 102(e) Date: Nov. 15, 1994

[87] PCT Pub. No.: WO93/24482

PCT Pub. Date: Dec. 9, 1993

[30] Foreign Application Priority Data

May 29, 1992 [DE] Germany .......................... 42 17 719.7

[51] Int. Cl.$^6$ .......................... A01N 43/66; A01N 43/54; C07D 239/42; C07D 251/40

[52] U.S. Cl. .......................... 504/230; 504/231; 504/239; 504/242; 504/273; 504/283; 504/289; 544/212; 544/219; 544/296; 544/298; 544/320; 544/331; 548/263.4; 548/518

[58] Field of Search .................................... 504/230, 231, 504/239, 242, 273, 283, 289, 210, 211; 544/212, 219, 296, 298, 320, 331, 297; 548/518, 263.4; 549/68, 71; 540/354, 355, 359

[56] References Cited

U.S. PATENT DOCUMENTS

| | | | |
|---|---|---|---|
| 4,401,816 | 8/1983 | Levitt | 544/320 |
| 4,515,620 | 5/1985 | Bohner | 544/209 |
| 4,743,292 | 5/1988 | Hay et al. | 544/324 |
| 4,842,639 | 6/1989 | Pasteris | 544/198 |
| 5,030,270 | 7/1991 | Loher et al. | 544/319 |
| 5,129,941 | 7/1992 | Loher et al. | 544/319 |

FOREIGN PATENT DOCUMENTS

| | | |
|---|---|---|
| 0171286 | 2/1986 | European Pat. Off. . |
| 0177163 | 4/1986 | European Pat. Off. . |
| 0238070 | 9/1987 | European Pat. Off. . |
| 0353641 | 2/1990 | European Pat. Off. . |
| 0409114 | 1/1991 | European Pat. Off. . |

OTHER PUBLICATIONS

Trueb, CA99:105288, 1983.

Patent Abstracts of Japan, JP60214785, Oct. 28, 1985, vol. 010078 (Mar. 27, 1986); "Pyrazolesulfonyl Urea Derivative and Plant Growth . . . ", Y. Susumu et al; 1 pg.

Derwent Abstract, JP58015962A, Jan. 29, 1983, Week 8310; "Sulphonyl-ureide derivatives with herbicidal and fungicidal . . . ", Mitsui Toatsu Chem Inc; 2 pages.

*Primary Examiner*—Yogendra N. Gupta

*Attorney, Agent, or Firm*—Sprung Horn Kramer & Woods

[57] ABSTRACT

The invention relates to new heterocyclically disubstituted sulphonylamino(thio)carbonyl compounds of the formula (I)

$$R^1-SO_2-NH-\overset{\overset{Q}{\|}}{C}-R^2 \qquad (I)$$

in which

Q represents oxygen or sulphur, $R^1$ and $R^2$ are identical or different and independently of one another represent a radical from the series comprising heterocyclyl, heterocyclylamino and heterocyclylimino, in each case optionally substituted and bonded via N, with the exception of optionally substituted pyrazolylamino in the meaning of $R^1$, and salts of the compounds of the formula (I), furthermore to processes for their preparation, and to their use as herbicides.

4 Claims, No Drawings

HETEROCYCLICALLY DISUBSTITUTED SULPHONYLAMINO(THIO)CARBONYL COMPOUNDS

This application is A 371 of PCT/EP93/01227 filed on May 17, 1993.

The invention relates to new heterocyclically disubstituted sulphonylamino(thio)carbonyl compounds, to a plurality of processes for their preparation, and to their use as herbicides.

It has been disclosed that certain heterocyclically disubstituted sulphamoyl ureas, such as, for example, 1-(4,6-dimethoxy-pyrimidin-2-yl)-3-(1-methyl-4-ethoxycarbonyl-purazol-5-yl-aminosulphonyl)-urea, have herbicidal properties (cf. JP-A 60214785 - cited in Chem. Abstracts 104: 109685u; cf. also U.S. Pat. No. 4515620). However, compounds of the abovementioned publications have, as yet, not gained a position of particular importance.

New heterocyclically disubstituted sulphonylamino(thio)-carbonyl compounds of the general formula (I), $$R^1-SO_2-NH-\overset{\overset{\displaystyle Q}{\|}}{C}-R^2 \qquad (I)$$

in which

Q represents oxygen or sulphur, $R^1$ and $R^2$ are identical or different and independently of one another represent a radical from the series comprising heterocyclyl, heterocyclylamino and heterocyclylimino, each of which is optionally substituted and bonded via N, with the exception of (optionally substituted) pyrazolylamino in the meaning of $R^1$, and salts of the compounds of the formula (I) have now been found.

The new heterocyclically disubstituted sulphonylamino(thio)carbonyl compounds of the general formula (I) and, if appropriate, their salts are obtained when (a) heterocycles of the general formula (II)

$$H-R^2 \qquad (II)$$

in which $R^2$ has the abovementioned meaning are reacted with chlorosulphonyl iso(thio)cyanate of the formula (III)

$$Cl-SO_2-N=C=Q \qquad (III)$$

in which

Q has the abovementioned meaning, if appropriate in the presence of an acid acceptor and if appropriate in the presence of a diluent (step 1), and the resulting chlorosulphonylamino(thio)carbonyl compounds of the general formula (IV)

$$Cl-SO_2-NH-\overset{\overset{\displaystyle Q}{\|}}{C}-R^2 \qquad (IV)$$

in which

Q and $R^2$ have the abovementioned meaning are reacted with heterocycles of the general formula (V)

$$R^1-H \qquad (V)$$

in which $R^1$ has the abovementioned meaning, if appropriate in the presence of an acid acceptor and if appropriate in the presence of a diluent (step 2), or when (b) heterocycles of the general formula (V)

$$R^1-H \qquad (V)$$

in which $R^1$ has the abovementioned meaning are reacted with oxysulphonylamino(thio)carbonyl compounds of the general formula (VI)

$$R^4-O-SO_2-NH-\overset{\overset{\displaystyle Q}{\|}}{C}-R^2 \qquad (VI)$$

in which

Q and $R^2$ have the abovementioned meaning and $R^4$represents alkyl (preferably methyl), haloalkyl (preferably trichloroethyl) or aryl (preferably phenyl), if appropriate in the presence of an acid acceptor and if appropriate in the presence of a diluent, or when (c) in the event that, in formula (I),

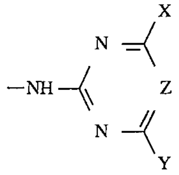

in which

X and Y are identical or different and independently of one another represent hydrogen, halogen, hydroxyl, amino, or in each case optionally substituted alkyl, alkoxy, alkylthio, alkylamino or dialkyl amino, and Z represents nitrogen or the group C-$Z^1$ in which $Z^1$ represents hydrogen, halogen or in each case optionally substituted alkyl or alkoxy, azinothiatriazine dioxides of the general formula (VII)

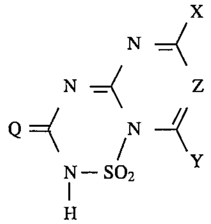
(VII)

in which

X, Y and Z have the abovementioned meaning are reacted with heterocycles of the general formula (V)

$$R^1-H \qquad (V)$$

in which $R^1$ has the abovementioned meaning, if appropriate in the presence of an acid acceptor and if appropriate in the presence of a diluent, and, if appropriate, the compounds of the formula (I) obtained by process (a), (b) or (c) are converted into salts by customary methods.

The new heterocyclically disubstituted sulphonylamino(thio) carbonyl compounds of the formula (I) are distinguished by a powerful herbicidal activity.

Other methods which are possible for the preparation of the compounds of the formula (I) according to the invention are given below, Q, $R^1$ and $R^2$ having the abovementioned meanings:

(d) reaction of heterocycles of the formula (V) with sulphamoyl chloride (VIII) and then with oxy(thio)carbonyl compounds of the formula (IX), ($R^4$: alkyl, aryl):

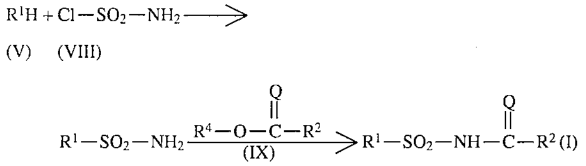

(c) reaction of heterocycles of the formula (V) with sulphamoyl chloride (VIII) and then with iso(thio)cyanates of the formula (X), (Het: heterocyclyl):

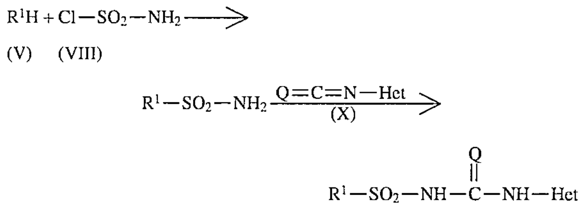

(f) reaction of heterocycles having exchangeable groups of the formula (XI) with sulphamide of the formula (XII) and (thio)urethanes of the formula (XIII), (Het: heterocyclyl, $X^1$: halogen, if appropriate also alkylsulphonyl, $R^4$: alkyl, aryl):

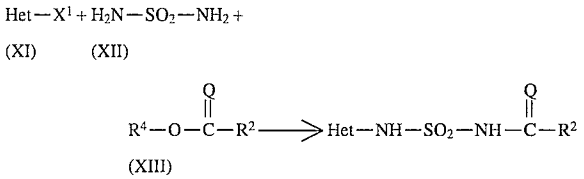

(g) reaction of heterocycles having exchangeable groups of the formula (XI) with sulphamide of the formula (XII) and iso(thio)cyanates (XIV), (Het: heterocyclyl, $X^1$: halogen, if appropriate also methylsulphonyl):

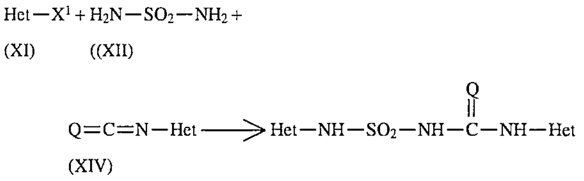

(h) reaction of heterocycles having exchangeable groups of the formula (XI) with sulphamide of the formula (XII), then with chloro(thio)formic esters of the formula (XV) and finally with heterocycles of the formula (II), (Het: heterocyclyl, $X^1$: halogen, if appropriate also alkylsulphonyl, $R^4$: alkyl, aryl):

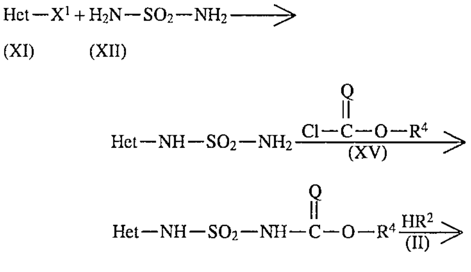

-continued

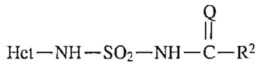

(i) reaction of heterocycles of the formula (V) and (thio-)carbamoyl compounds of the formula (XVI) with sulphuryl chloride:

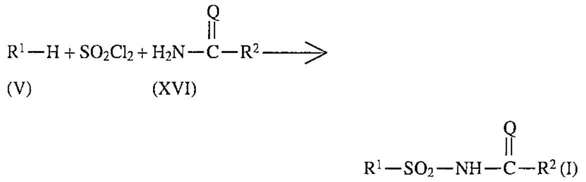

(j) reaction of sulphonyl iso(thio)cyanates of the formula (XVII) with ammonia and then with heterocyclyl halides of the formula (XI), (Het: heterocyclyl, $X^1$: halogen, if appropriate also alkylsulphonyl):

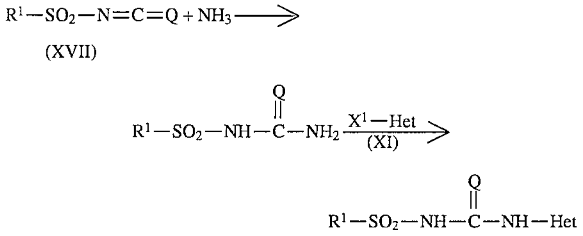

(k) reaction of chlorosulphonylamino(thio)carbonyl compounds of the formula (IV)—cf. process (a)—with ammonia and then with heterocyclyl halides of the formula (XI), (Het: heterocyclyl, $X^1$:halogen, if appropriate also alkylsulphonyl):

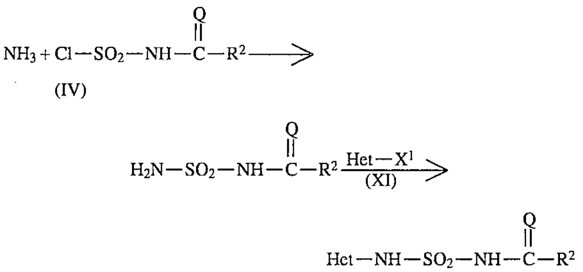

The invention preferably relates to compounds of the formula (I) in which

Q represents oxygen or sulphur, $R^1$represents a radical from the series comprising heterocyclyl, heterocyclylamino (with the exception of pyrazolylamino) and heterocyclylimino, optionally substituted and bonded via N, where heterocyclyl (also in heterocyclyl-amino or -imino) represents a monocyclic, bicyclic or spiro-cyclic, saturated or unsaturated heterocyclic group having a total of 3 to 14 ring members of which at least one is a heteroatom from the series comprising N, O or S, it also being possible for the heterocyclic group to contain 1 to 3 groups from the series comprising

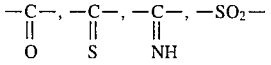

as ring members, and $R^2$ represents a radical from the series comprising heterocyclyl, heterocyclylamino and heterocyclylimino, optionally substituted and bonded via N, where heterocyclyl represents a monocyclic or bicyclic, saturated or unsaturated heterocyclic group having a total of 4 to 10 ring members of which at least one is an N, or S atom, it also being possible for the heterocyclic group to contain 1 to 3 groups from the series comprising

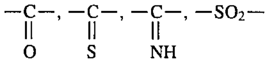

as ring members, and the substituents which are possible for $R^1$ and $R^2$ are furthermore preferably selected from the series comprising: halogen, cyano, nitro, carboxyl, carbamoyl, amino, hydroxyl, formyl, or $C_1$–$C_6$-alkyl, $C_5$–$C_6$-alkanediyl, $C_2$–$C_6$-alkenyl, $C_2$–$C_6$-alkinyl, $C_3$–$C_6$-cycloalkyl, $C_3$–$C_6$-cycloalkyl-$C_1$–$C_4$-alkyl, $C_1$–$C_6$-alkoxy, $C_2$–$C_6$-alkenyloxy, $C_2$–$C_6$-alkinyloxy, $C_1$–$C_6$-alkylthio, $C_2$–$C_6$-alkenylthio, $C_2$–$C_6$-alkinylthio, $C_1$–$C_6$-alkylsulphinyl, $C_1$–$C_6$-alkylsulphonyl, $C_1$–$C_6$-alkylamino, di-($C_1$–$C_4$-alkyl)-amino, $C_1$–$C_6$-alkyl-carbonyl, $C_3$–$C_6$-cycloalkyl-carbonyl, $C_1$–$C_6$-alkoxy-carbonyl, $C_1$–$C_4$-alkoxy-$C_1$–$C_4$-alkoxy-carbonyl, di-($C_1$–$C_4$-alkyl)-aminocarbonyl, di-($C_1$–$C_4$-alkoxy)-phosphoryl or di-($C_1$–$C_4$-alkoxy)-thiophosphoryl, each of which is optionally substituted by halogen, or phenyl, phenoxy, phenylthio, phenylsulphinyl, phenylsulphonyl, phenyl-$C_1$–$C_4$-alkyl or phenyl-$C_2$–$C_4$-alkenyl, each of which is optionally substituted by halogen, cyano, nitro, carboxyl, carbamoyl, amino, hydroxyl, formyl, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-alkylsulphinyl, $C_1$–$C_4$-alkylsulphonyl, $C_1$–$C_4$-halogenoalkylthio, $C_1$–$C_4$-halogenoalkylsulphinyl, $C_1$–$C_4$-halogenoalkylsulphonyl and/or $C_1$–$C_4$-alkoxy-carbonyl.

In particular, the invention relates to compounds of the formula (I) in which

Q represents oxygen or sulphur, $R^1$ represents a radical of the series comprising heterocyclyl, heterocyclylamino, heterocyclylimino, optionally substituted and bonded via N, where heterocyclyl in these radicals represents a monocyclic, bicyclic or spirocyclic, saturated or unsaturated heterocyclic group from the series which follows:

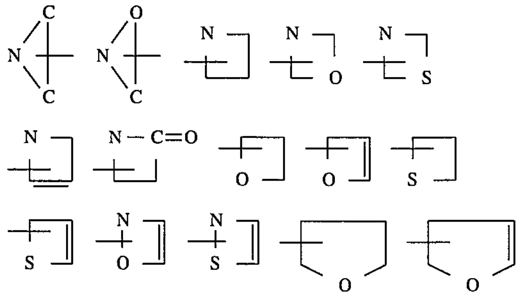

-continued

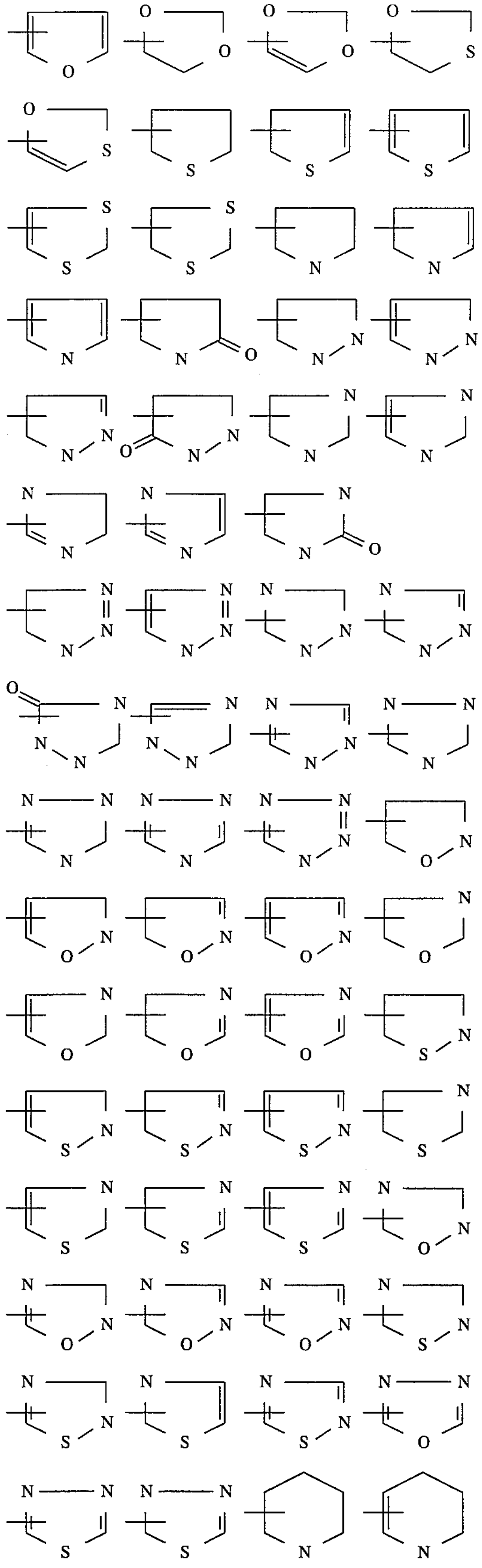

-continued
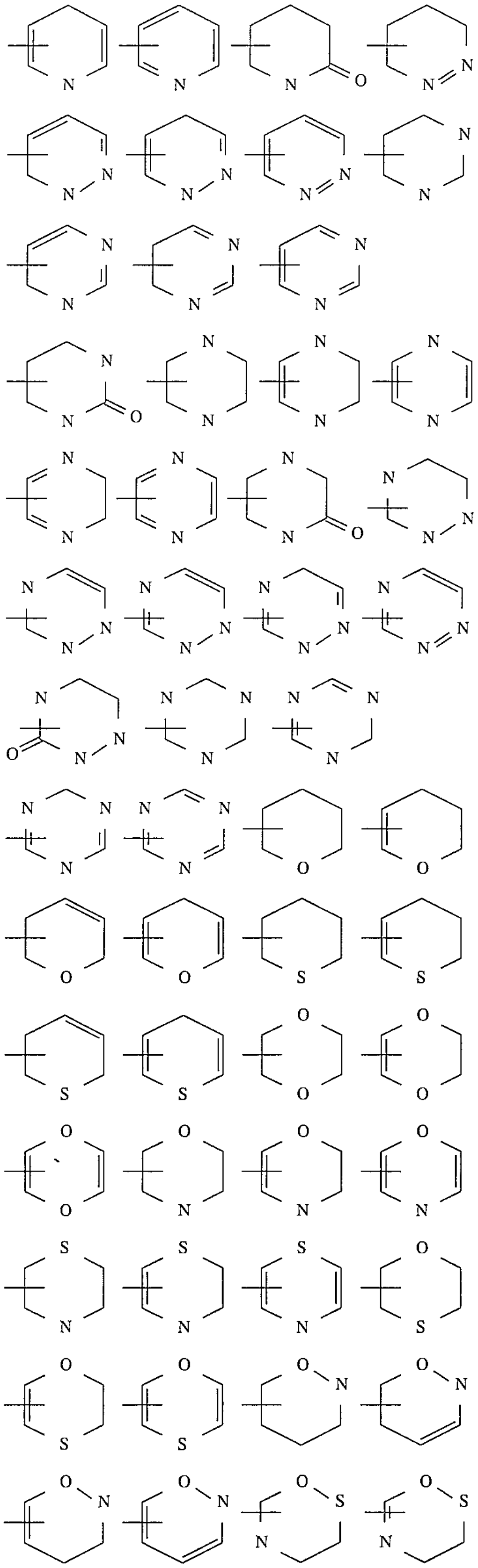
-continued
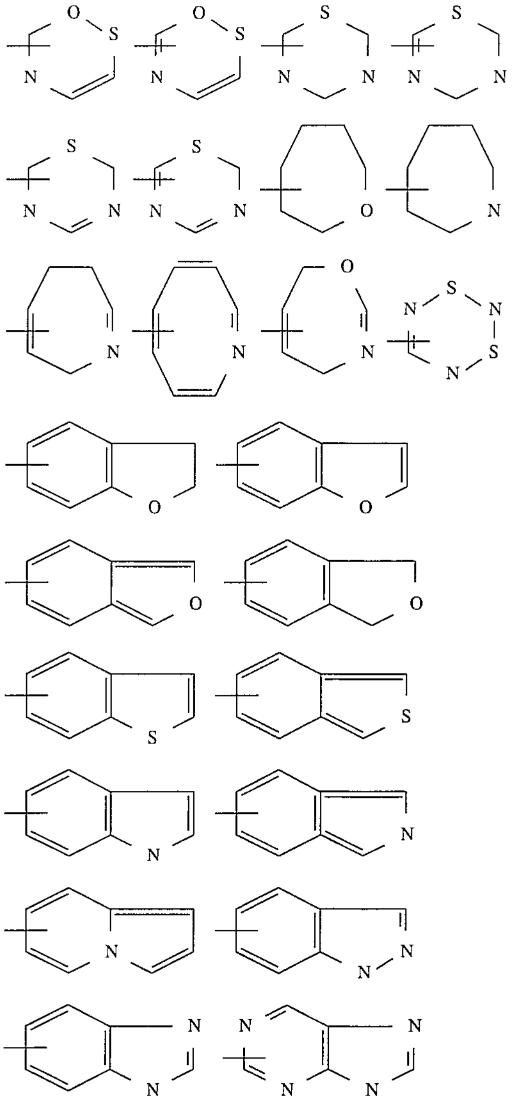
and
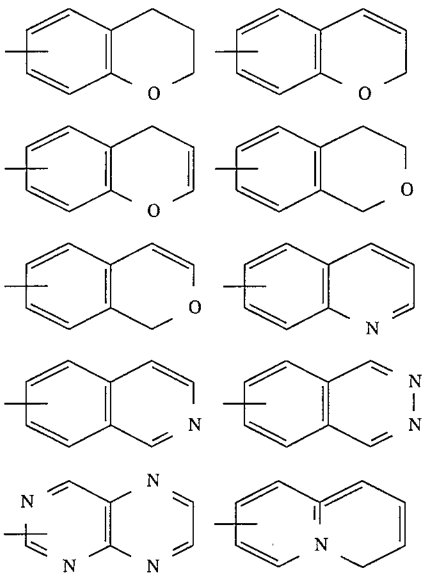

-continued
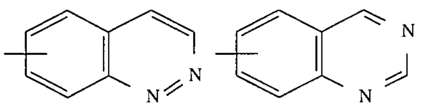
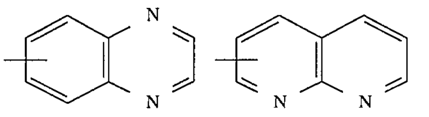
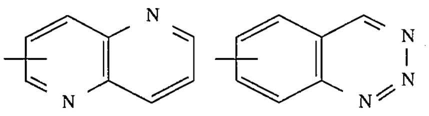
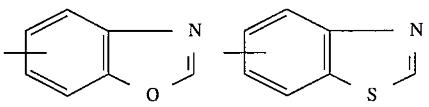
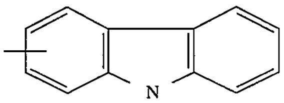
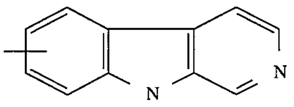
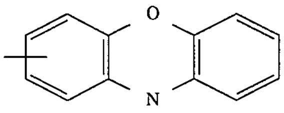
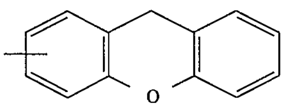
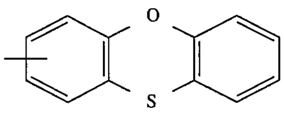
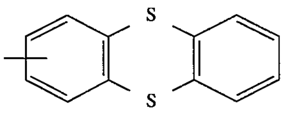
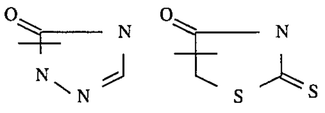
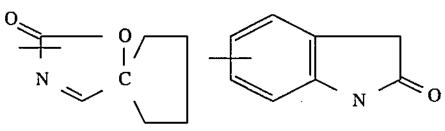
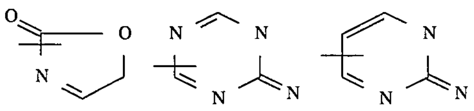
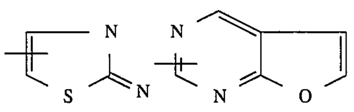
-continued
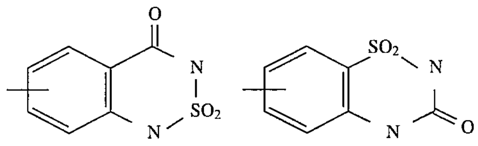
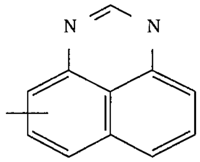
and
$R^2$ represents a radical from the series comprising heterocyclyl, heterocyclylamino and heterocyclylimino, optionally substituted and bonded via N, where heterocyclyl represents a monocyclic or bicyclic, saturated or unsaturated heterocyclic group from the series which follows:
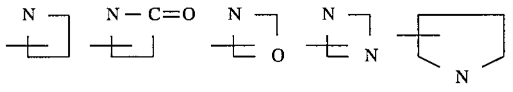
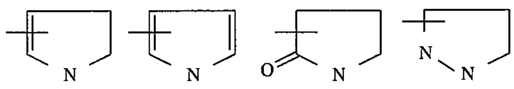
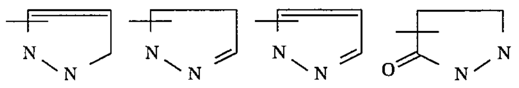
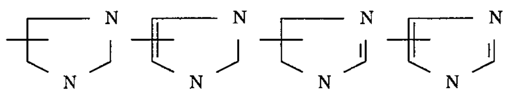
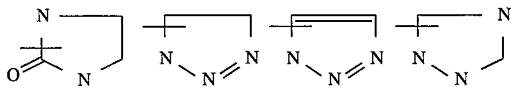
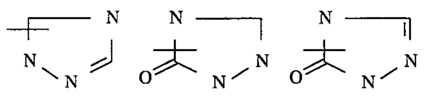
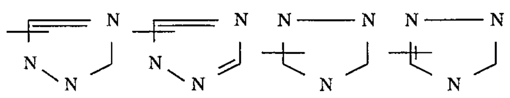
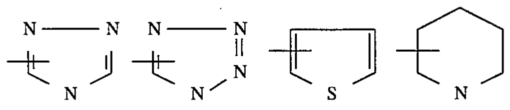
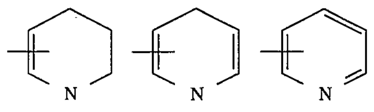
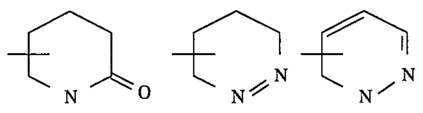
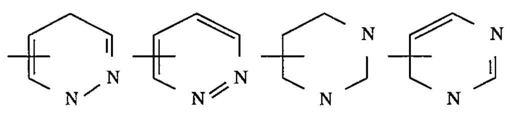

-continued

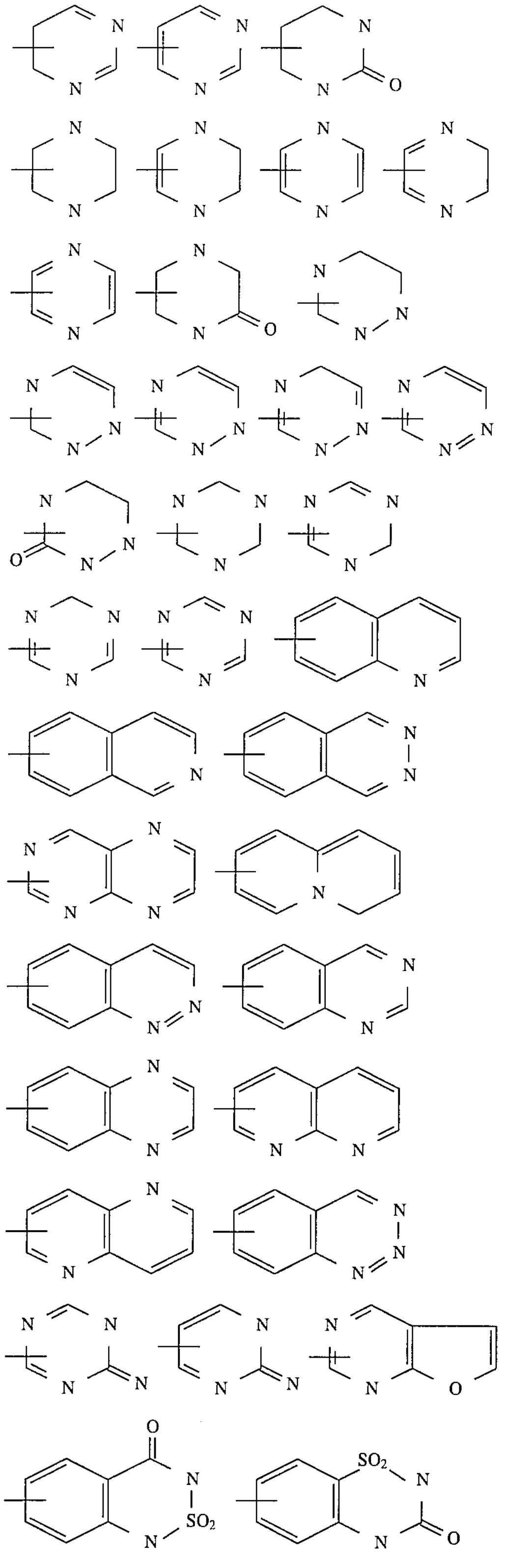

and the substituents which are possible for $R^1$ and $R^2$ are furthermore selected in particular from the series comprising:

fluorine, chlorine, bromine, iodine, cyano, nitro, carboxyl, carbamoyl, amino, hydroxyl, formyl, or $C_1$–$C_5$-alkyl, $C_5$–$C_6$-alkanediyl, $C_2$–$C_5$-alkenyl, $C_2$–$C_5$-alkinyl, $C_3$–$C_6$-cycloalkyl, $C_3$–$C_6$-cycloalkyl-$C_1$–$C_3$-alkyl, $C_1$–$C_5$-alkoxy, $C_2$–$C_5$-alkenyloxy, $C_2$–$C_5$-alkinyloxy, $C_1$–$C_5$-alkenylthio, $C_2$–$C_5$-alkenylthio, $C_2$–$C_5$-alkinylthio, $C_1$–$C_5$-alkylsulphinyl, $C_1$–$C_5$-alkylsulphonyl, $C_1$–$C_5$-alkylamino, di-($C_1$–$C_3$-alkyl)-amino, $C_1$–$C_5$-alkyl-carbonyl, $C_3$–$C_6$-cycloalkyl-carbonyl, $C_1$–$C_5$-alkoxy-carbonyl, $C_1$–$C_2$-alkoxy-$C_1$–$C_2$-alkoxycarbonyl, di-($C_1$–$C_3$-alkyl)-amino-carbonyl, dimethoxyphosphoryl, diethoxyphosphoryl, dimethoxythiophosphoryl or diethoxythiophosphoryl, each of which is optionally substituted by fluorine and/or chlorine, or phenyl, phenoxy, phenylthio, phenylsulphinyl, phenylsulphonyl, phenyl-$C_1$–$C_3$-alkyl or phenyl-$C_2$–$C_3$-alkenyl, each of which is optionally substituted by fluorine, chlorine, bromine, iodine, cyano, nitro, carboxyl, carbamoyl, amino, hydroxyl, formyl, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl, $C_1$–$C_4$-alkylsulphonyl (each of which is optionally substituted by fluorine and/or chlorine) and/or $C_1$–$C_4$-alkoxycarbonyl.

Very particularly preferred groups of compounds of the formula (I) are those which follow:

(A) Q represents oxygen and
$R^1$ and $R^2$ are identical or different and in each case represent pyrimidine-2-yl-amino or 1,3,5-triazine-2-yl-amino, each of which is optionally substituted by fluorine, chlorine, bromine, methyl, ethyl, propyl, isopropyl, cyclopropyl, methoxy, ethoxy, propoxy, isopropoxy, chloromethyl, dichloromethyl, trichloromethyl, fluoromethyl, difluoromethyl, trifluoromethyl, methoxymethyl, ethoxymethyl, methoxyethyl, ethoxyethyl, difluoromethoxy, chloroethoxy, dichloroethoxy, trichloroethoxy, fluoroethoxy, difluoroethoxy, trifluoroethoxy, methylthio, ethylthio, methylamino, ethylamino or dimethylamino, it also being possible in each case for the amino group which links the heterocycle to be methylated;

(B) Q represents oxygen,
$R_1$ represents pyrimidine-2-yl-amino or 1,3,5-triazine-2-yl-amino, both of which can be substituted as given above under (A) , and
$R_2$ represents 2,4-dihydro-3H-1,2,4-triazole-3-on-2-yl which is optionally substituted by fluorine, chlorine, bromine, methyl, ethyl, propyl, isopropyl, butyl, isobutyl, sec-butyl, fluoromethyl, difluoromethyl, trifluoromethyl, chloromethyl, dichloromethyl, trichloromethyl, fluoroethyl, difluoroethyl, trifluoroethyl, chloroethyl, dichloroethyl, trichloroethyl, chlorodifluoromethyl, fluorodichloromethyl, chlorodifluoroethyl, trifluorochloroethyl, methoxy, ethoxy, propoxy, isopropoxy, butoxy, isobutoxy, sec-butoxy, methylthio, ethylthio,
propylthio, isopropylthio, butylthio, isobutylthio, sec-butylthio, amino, methylamino, ethylamino, propylamino, isopropylamino, butylamino, isobutylamino, sec-butylamino, dimethylamino, diethylamino, cyclopropyl, cyclobutyl, cyclopentyl or cyclohexyl;

(C) Q represents oxygen,
$R_1$ has the meaning given above under (B) for $R^2$ and
$R^2$ has the meaning given above under (B) for $R^1$;

(D) Q represents oxygen,
$R_1$ has the meaning given above as particularly preferred and
$R^2$ has the meaning given above under (A).

The invention furthermore preferably relates to salts which are obtained from compounds of the formula (I) with bases, such as, for example, sodium hydroxide, sodium hydride, sodium amide, sodium carbonate, potassium hydroxide, potassium hydride, potassium amide, potassium carbonate, calcium hydroxide, calcium hydride, calcium amide or calcium carbonate, sodium $C_1$–$C_4$ -alkanolates or potassium $C_1$–$C_4$-alkanolates, ammonia, $C_1$–$C_4$-alkylamines, di-($C_1$–$C_4$-alkyl)-amines or tri-($C_1$–$C_4$-alkyl)-amines.

The abovementioned definitions of radicals, in general or in preferred ranges, apply to the end products of the formula (I) and, analogously, to the starting materials or intermediates required in each case for the preparation. These definitions of radicals can be combined with each other as desired, that is to say any desired combination between the preferred ranges which have been given is also possible.

The hydrocarbon radicals which have been mentioned in the definitions of radicals, such as alkyl, alkenyl or alkinyl, also in combination with heteroatoms, such as in alkoxy, alkylthio or alkylamino, are straight-chain or branched even when not expressly stated.

Halogen generally represents fluorine, chlorine, bromine or iodine, preferably fluorine, chlorine or bromine, in particular fluorine or chlorine.

Examples of the compounds of the formula (I) according to the invention are listed in Table 1 which follows.

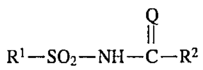

(I)

TABLE 1

| Q | $R^1$ | $R^2$ |
|---|---|---|
| | Examples of the compounds of the formula (I) | |
| O | 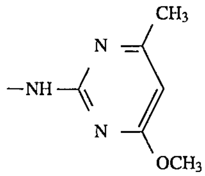 | 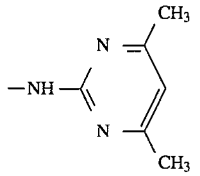 |
| S | 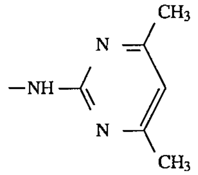 | 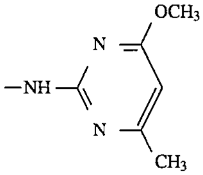 |
| O | 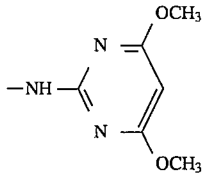 | 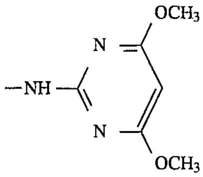 |
| S | 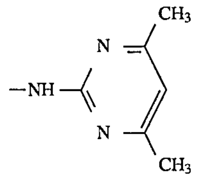 | 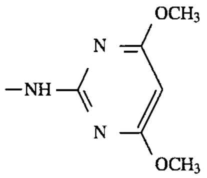 |

TABLE 1-continued

| Q | $R^1$ | $R^2$ |
|---|---|---|
| | Examples of the compounds of the formula (I) | |
| O | 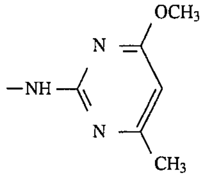 | 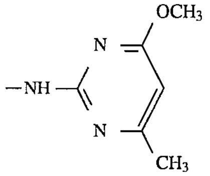 |
| S | 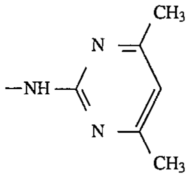 | 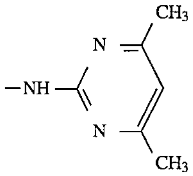 |
| O | 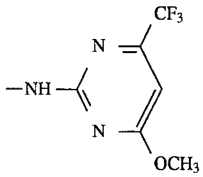 | 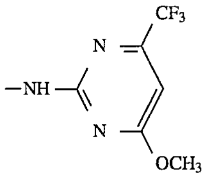 |
| O | 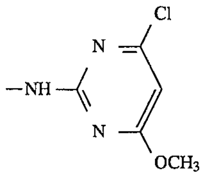 | 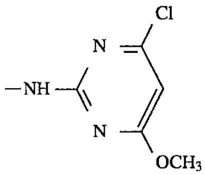 |
| O | 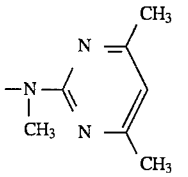 | 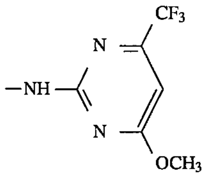 |
| O | 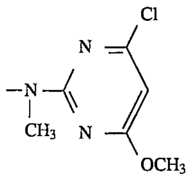 | 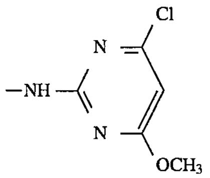 |
| O | 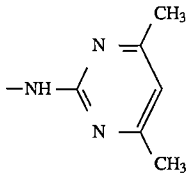 | 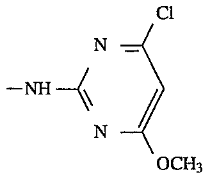 |
| O | 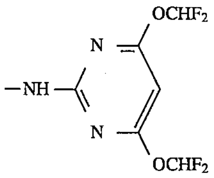 | 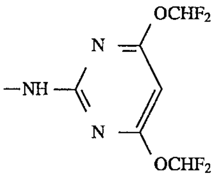 |

TABLE 1-continued
| Examples of the compounds of the formula (I) | | |
|---|---|---|
| Q | R[1] | R[2] |
| O | 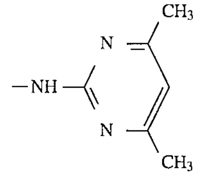 | 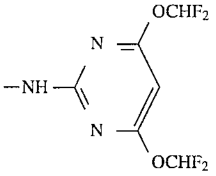 |
| O | 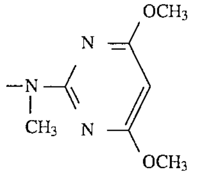 | 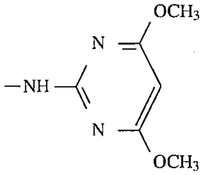 |
| O | 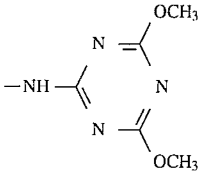 | 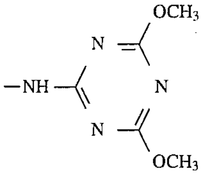 |
| S | 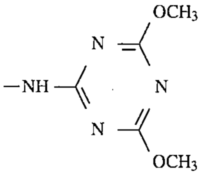 | 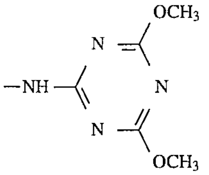 |
| O | 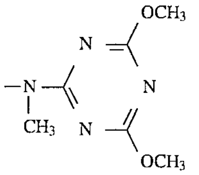 | 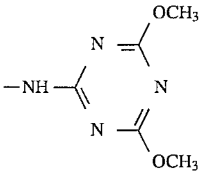 |
| O | 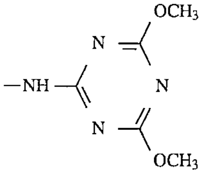 | 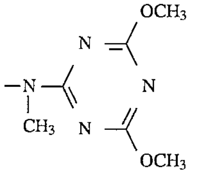 |
| O | 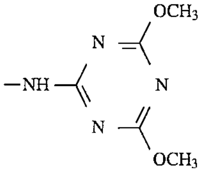 | 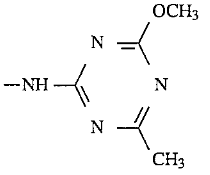 |
| O | 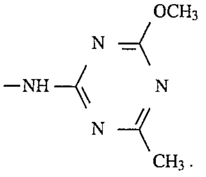 | 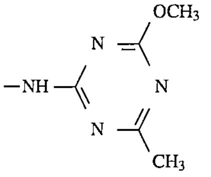 |
TABLE 1-continued
| Examples of the compounds of the formula (I) | | |
|---|---|---|
| Q | R[1] | R[2] |
| O | 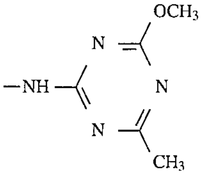 | 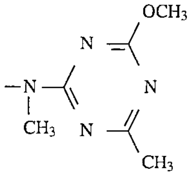 |
| O | 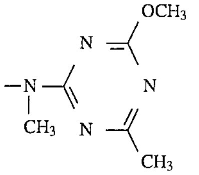 | 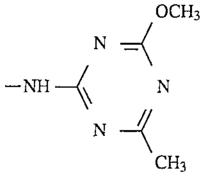 |
| O | 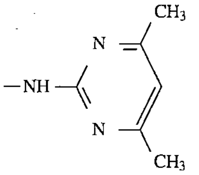 | 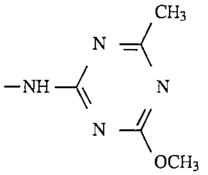 |
| O | 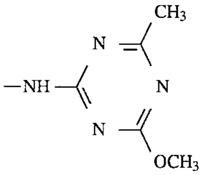 | 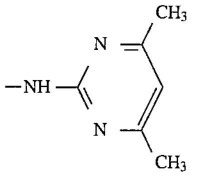 |
| O | 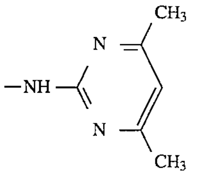 | 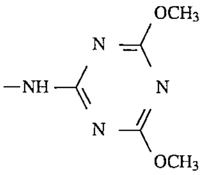 |
| O | 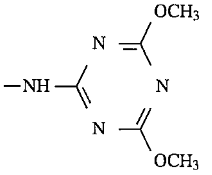 | 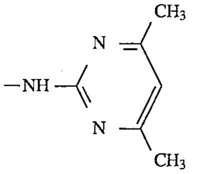 |
| O | 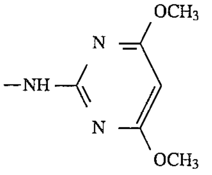 | 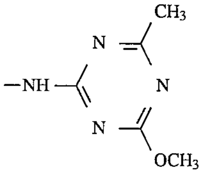 |
| O | 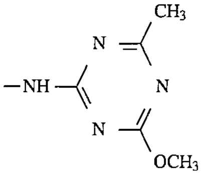 | 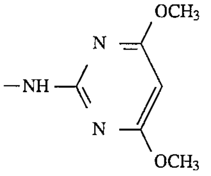 |

TABLE 1-continued
| Examples of the compounds of the formula (I) | | |
|---|---|---|
| Q | $R^1$ | $R^2$ |
| O | 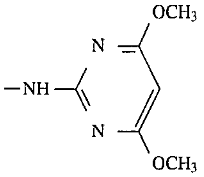 | 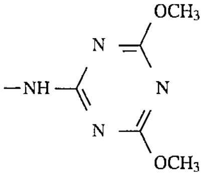 |
| O | 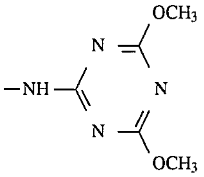 | 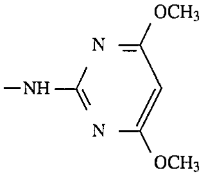 |
| O | 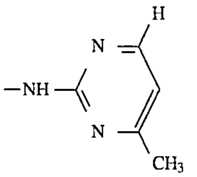 | 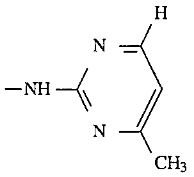 |
| O | 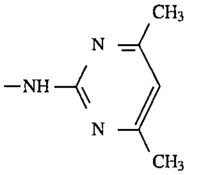 | 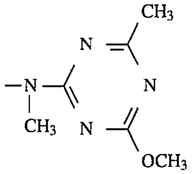 |
| O | 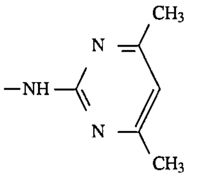 | 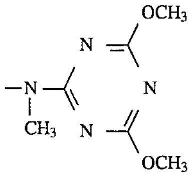 |
| O | 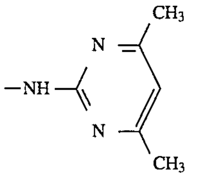 | 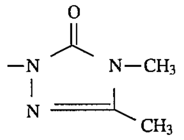 |
| O | 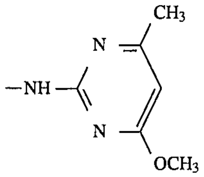 | 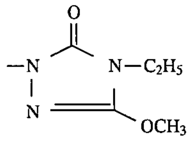 |
| O | 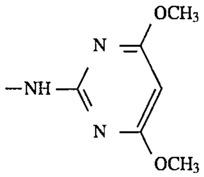 | 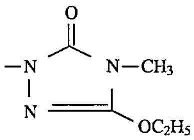 |
TABLE 1-continued
| Examples of the compounds of the formula (I) | | |
|---|---|---|
| Q | $R^1$ | $R^2$ |
| O | 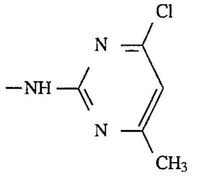 | 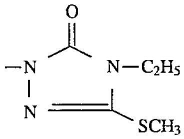 |
| O | 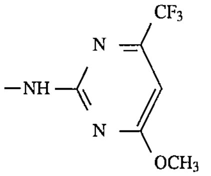 | 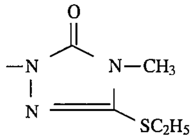 |
| O | 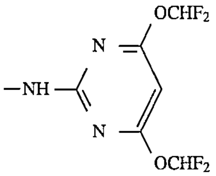 | 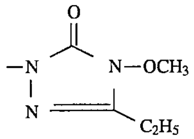 |
| O | 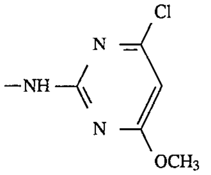 | 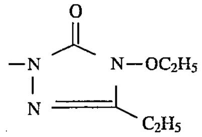 |
| O | 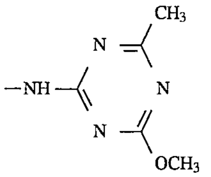 | 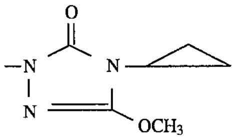 |
| O | 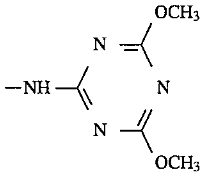 | 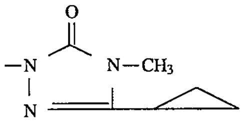 |
| O | 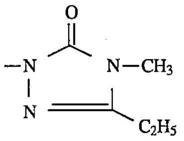 | 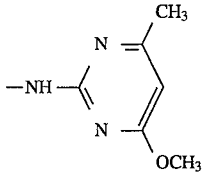 |
| O | 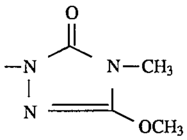 | 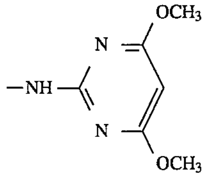 |

TABLE 1-continued
| Examples of the compounds of the formula (I) | | |
|---|---|---|
| Q | R[1] | R[2] |
| O | 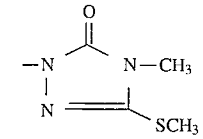 | 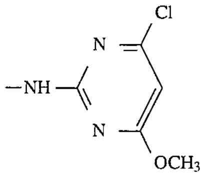 |
| O | 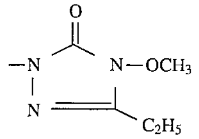 | 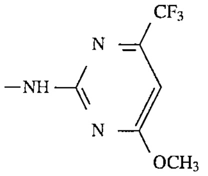 |
| O | 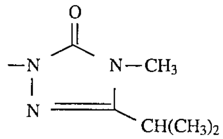 | 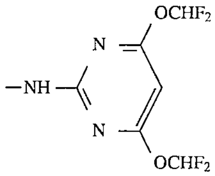 |
| O | 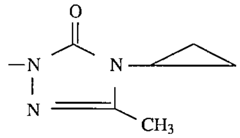 | 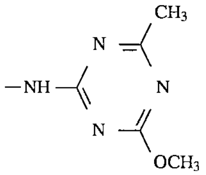 |
| O | 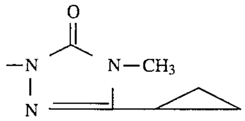 | 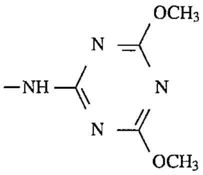 |
| O | 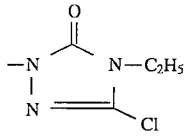 | 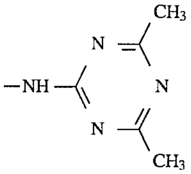 |
| O | 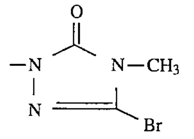 | 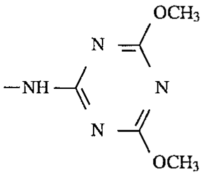 |
| O | 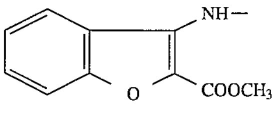 | 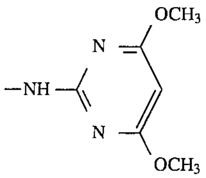 |
TABLE 1-continued
| Examples of the compounds of the formula (I) | | |
|---|---|---|
| Q | R[1] | R[2] |
| S | 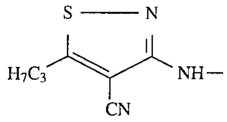 | 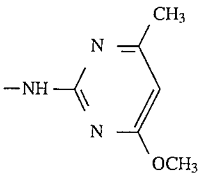 |
| O | 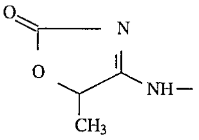 | 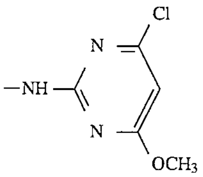 |
| O | 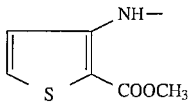 | 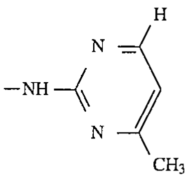 |
| O | 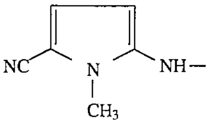 | 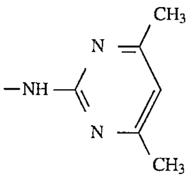 |
| S | 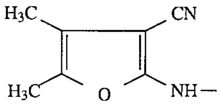 | 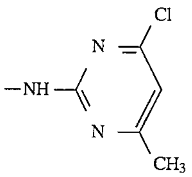 |
| O | 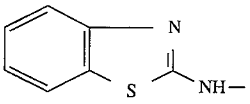 | 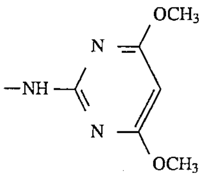 |
| O | 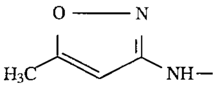 | 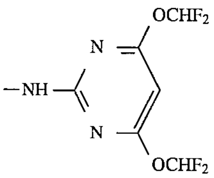 |
| O | 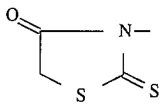 | 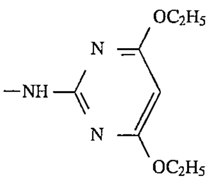 |

TABLE 1-continued
| Examples of the compounds of the formula (I) | | |
|---|---|---|
| Q | $R^1$ | $R^2$ |
| O | 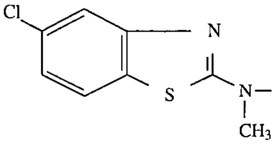 | 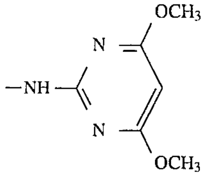 |
| O | 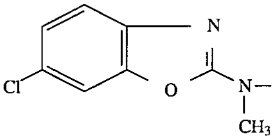 | 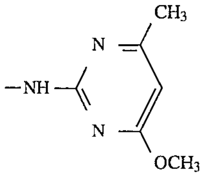 |
| O | 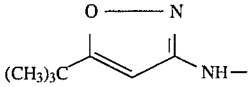 | 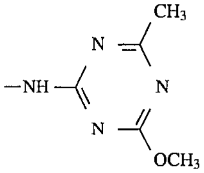 |
| O | 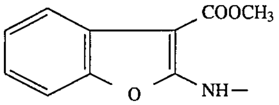 | 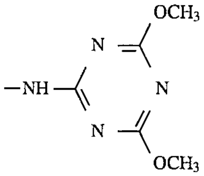 |
| O | 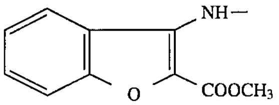 | 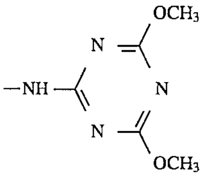 |
| O | 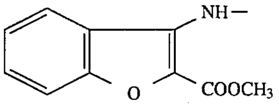 | 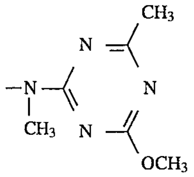 |
| O | 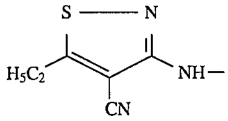 | 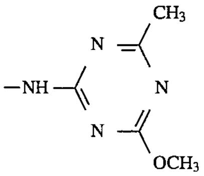 |
| O | 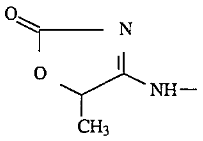 | 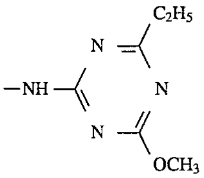 |
TABLE 1-continued
| Examples of the compounds of the formula (I) | | |
|---|---|---|
| Q | $R^1$ | $R^2$ |
| O | 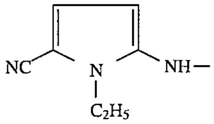 | 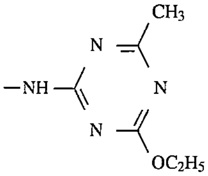 |
| O | 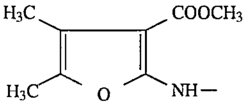 | 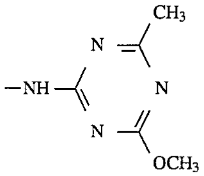 |
| O | 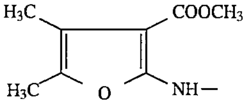 | 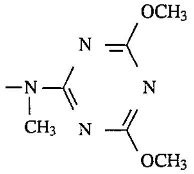 |
| O | 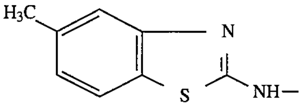 | 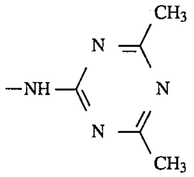 |
| S | 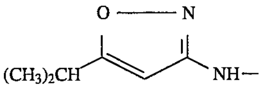 | 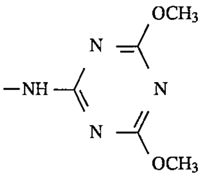 |
| O | 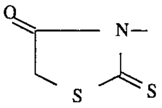 | 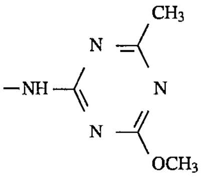 |
| O | 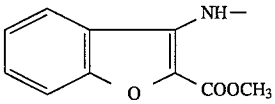 | 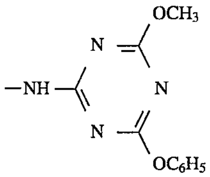 |
| O | 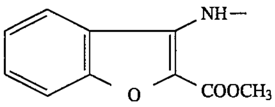 | 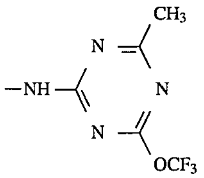 |

TABLE 1-continued
Examples of the compounds of the formula (I)
| Q | $R^1$ | $R^2$ |
|---|---|---|
| O | 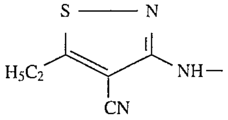 | 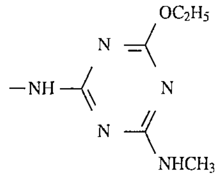 |
| O | 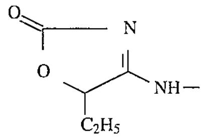 | 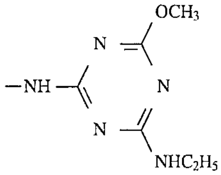 |
| S | 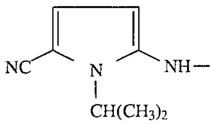 | 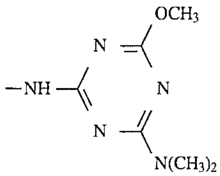 |
| O | 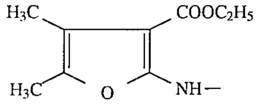 | 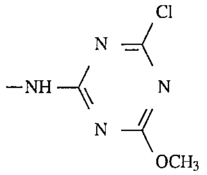 |
| O | 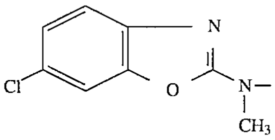 | 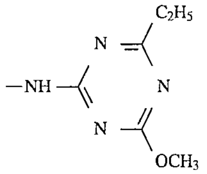 |
| O | 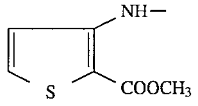 | 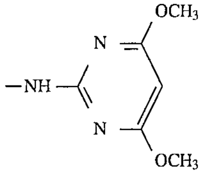 |
| O | 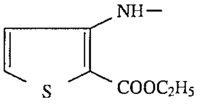 | 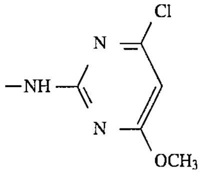 |
| O | 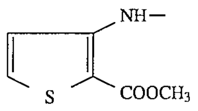 | 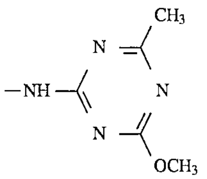 |
TABLE 1-continued
Examples of the compounds of the formula (I)
| Q | $R^1$ | $R^2$ |
|---|---|---|
| O | 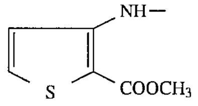 | 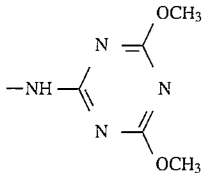 |
| O | 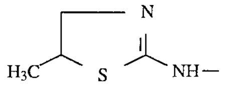 | 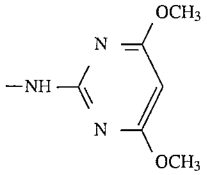 |
| O | 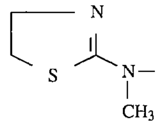 | 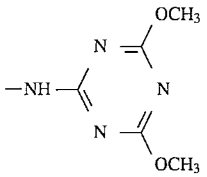 |
| S | 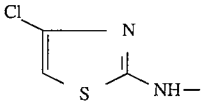 | 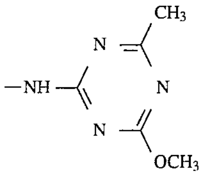 |
| O | 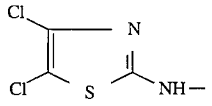 | 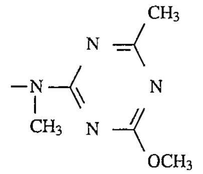 |
| O | 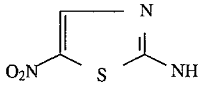 | 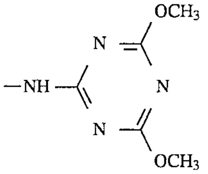 |
| O | 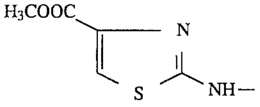 | 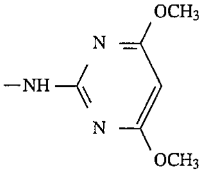 |
| O | 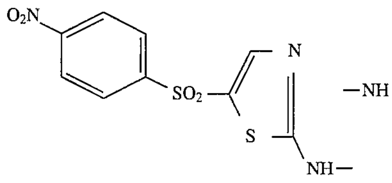 | 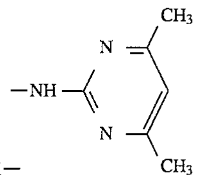 |

TABLE 1-continued
Examples of the compounds of the formula (I)
| Q | R[1] | R[2] |
|---|---|---|
| O | 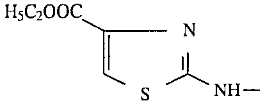 | 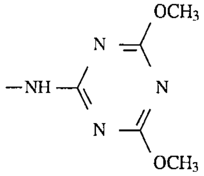 |
| O | 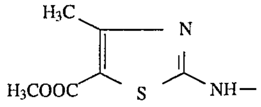 | 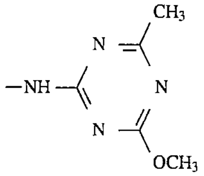 |
| O | 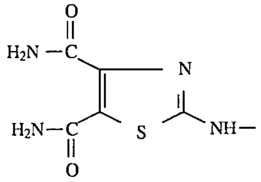 | 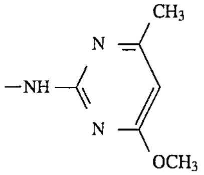 |
| S | 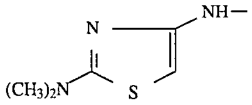 | 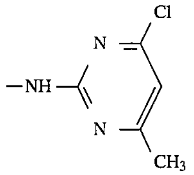 |
| O | 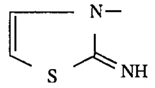 | 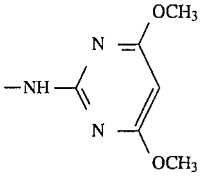 |
| O | 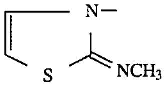 | 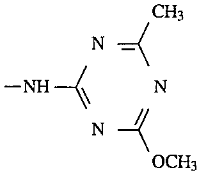 |
| O | 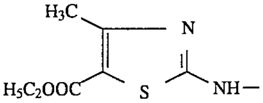 | 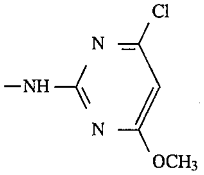 |
| O | 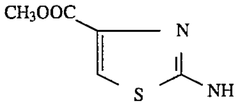 | 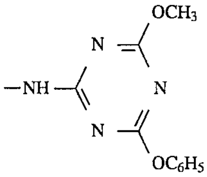 |
| O | 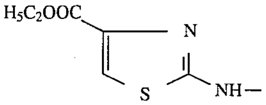 | 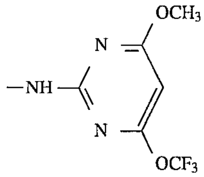 |
| S | 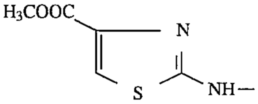 | 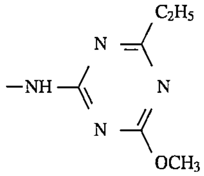 |
| O | 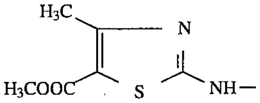 | 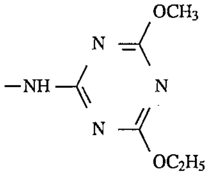 |
| O | 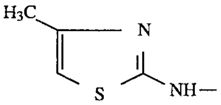 | 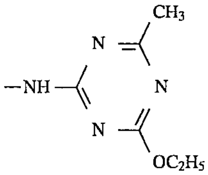 |
| O | 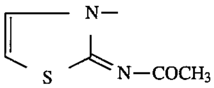 | 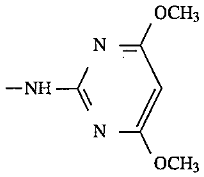 |
| S | 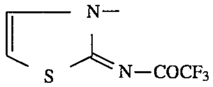 | 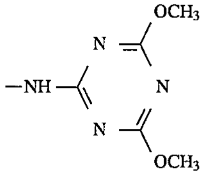 |
| O | 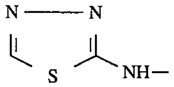 | 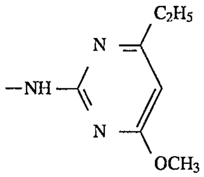 |

TABLE 1-continued
| Examples of the compounds of the formula (I) | | |
|---|---|---|
| Q | $R^1$ | $R^2$ |
| O | 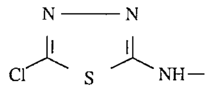 | 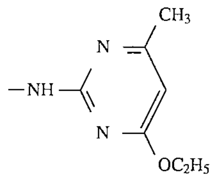 |
| O | 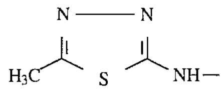 | 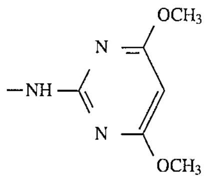 |
| O | 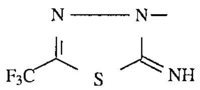 | 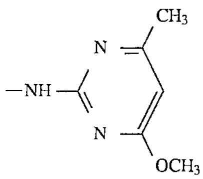 |
| O | 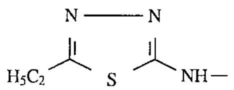 | 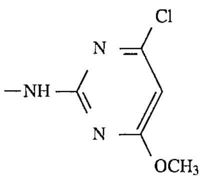 |
| O | 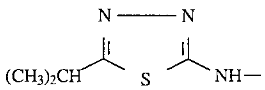 | 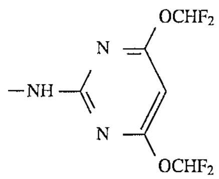 |
| O | 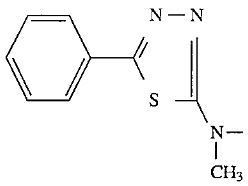 | 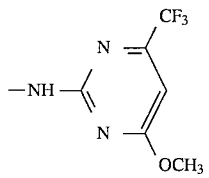 |
| O | 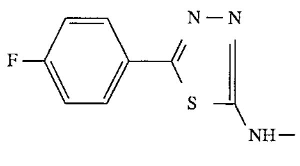 | 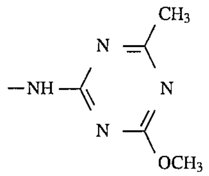 |
| O | 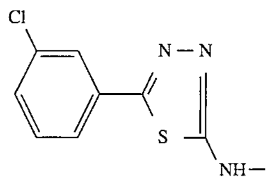 | 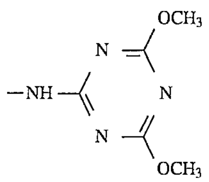 |
TABLE 1-continued
| Examples of the compounds of the formula (I) | | |
|---|---|---|
| Q | $R^1$ | $R^2$ |
| O | 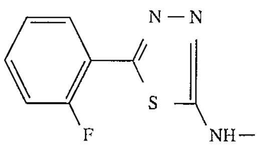 | 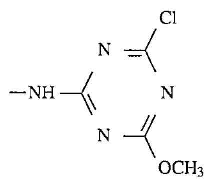 |
| O | 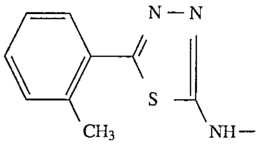 | 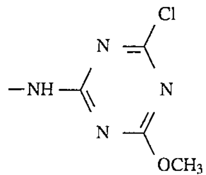 |
| S | 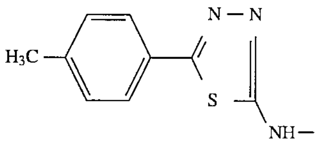 | 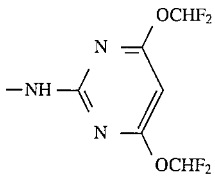 |
| O | 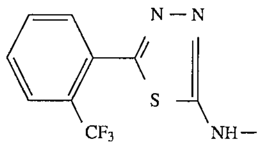 | 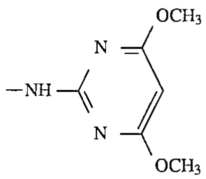 |
| O | 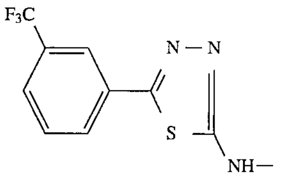 | 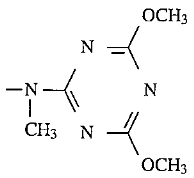 |
| O | 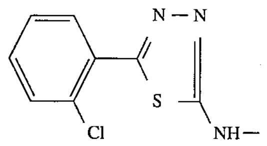 | 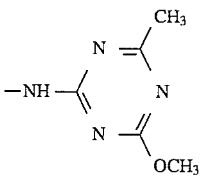 |
| O | 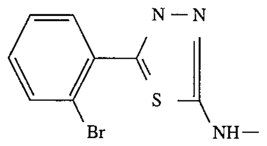 | 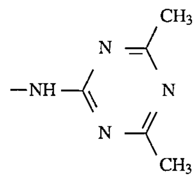 |

TABLE 1-continued
Examples of the compounds of the formula (I)
| Q | $R^1$ | $R^2$ |
| --- | --- | --- |
| O | 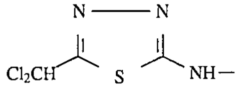 | 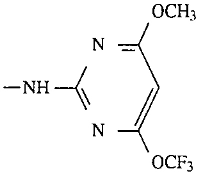 |
| O | 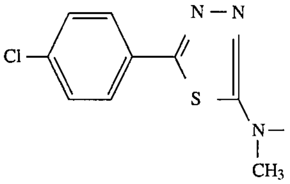 | 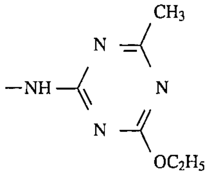 |
| O | 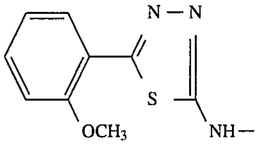 | 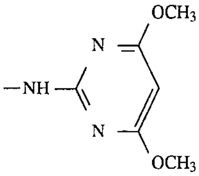 |
| O | 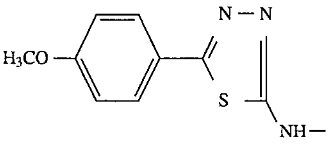 | 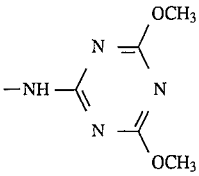 |
| S | 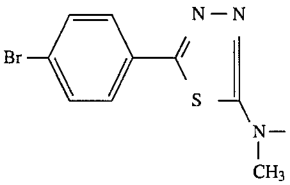 | 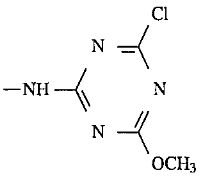 |
| O | 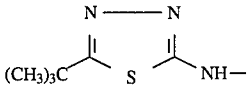 | 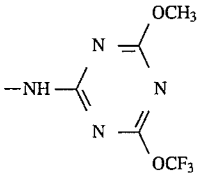 |
| O | 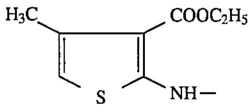 | 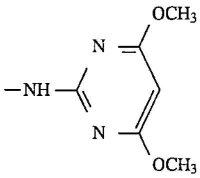 |
| O | 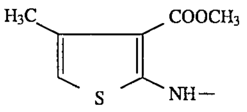 | 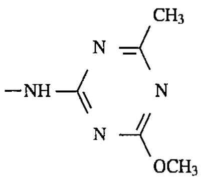 |
| S | 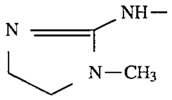 | 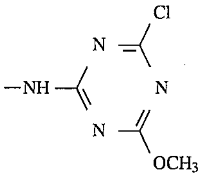 |
| O | 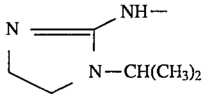 | 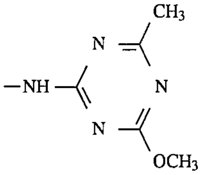 |
| O | 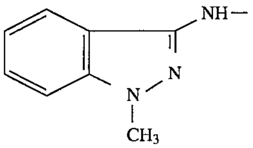 | 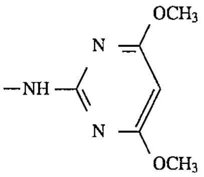 |
| O | 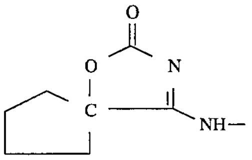 | 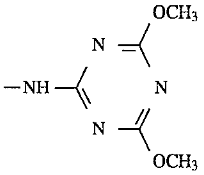 |
| O | 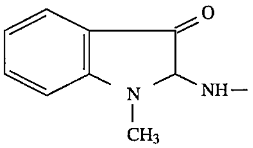 | 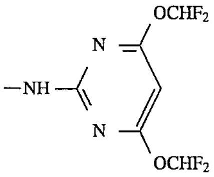 |
| O | 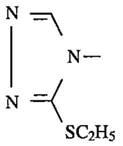 | 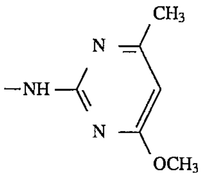 |
| O | 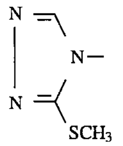 | 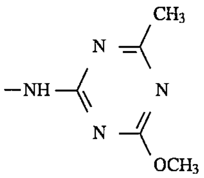 |

TABLE 1-continued
Examples of the compounds of the formula (I)
| Q | $R^1$ | $R^2$ |
| --- | --- | --- |
| O | 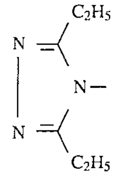 | 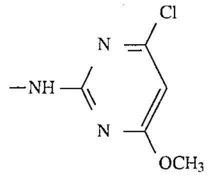 |
| S | 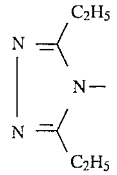 | 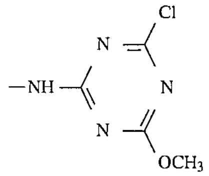 |
| O | 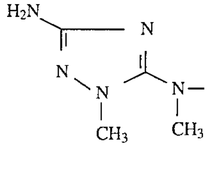 | 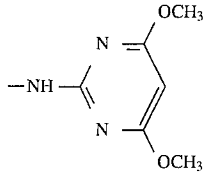 |
| O | 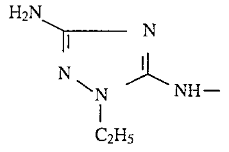 | 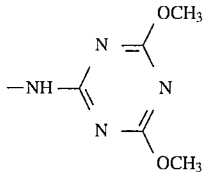 |
| O | 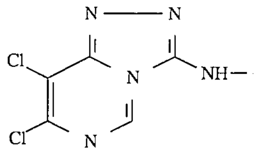 | 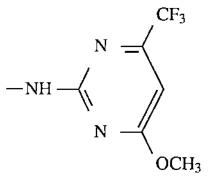 |
| O | 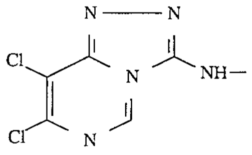 | 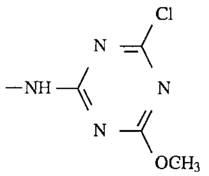 |
| O | 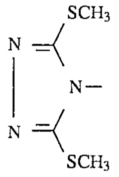 | 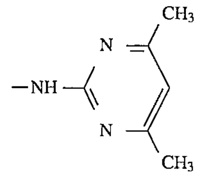 |
| O | 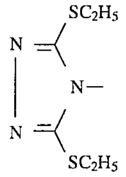 | 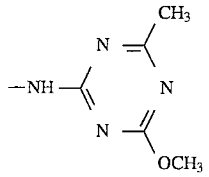 |
TABLE 1-continued
Examples of the compounds of the formula (I)
| Q | $R^1$ | $R^2$ |
| --- | --- | --- |
| O | 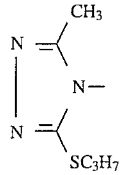 | 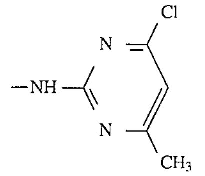 |
| O | 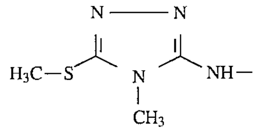 | 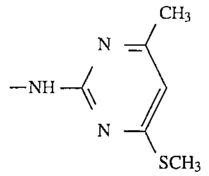 |
| O | 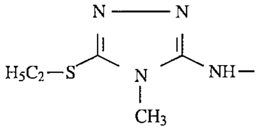 | 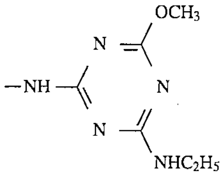 |
| S | 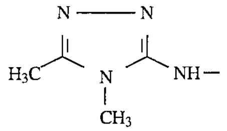 | 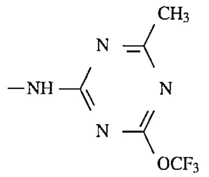 |
| O | 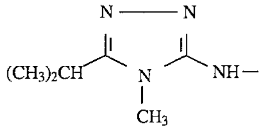 | 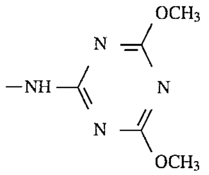 |
| O | 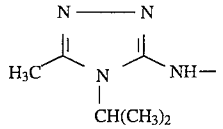 | 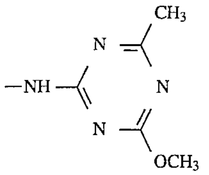 |
| O | 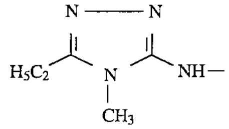 | 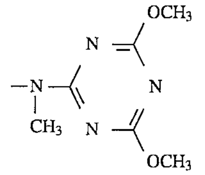 |
| S | 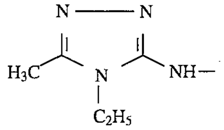 | 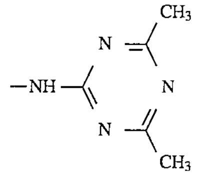 |

TABLE 1-continued
Examples of the compounds of the formula (I)
| Q | $R^1$ | $R^2$ |
|---|---|---|
| O | 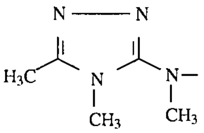 | 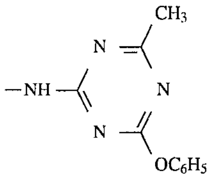 |
| O | 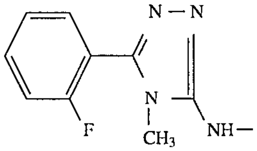 | 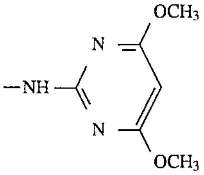 |
| O | 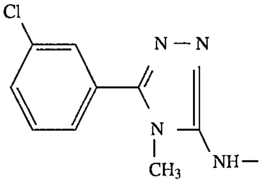 | 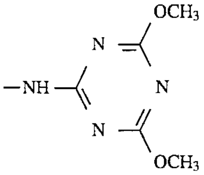 |
| O | 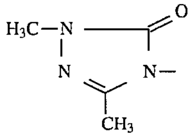 | 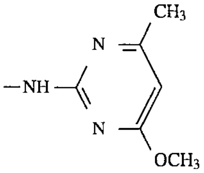 |
| O | 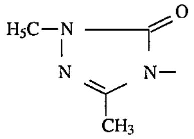 | 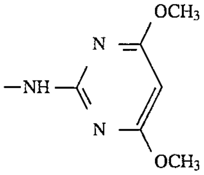 |
| S | 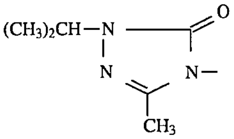 | 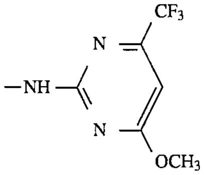 |
| O | 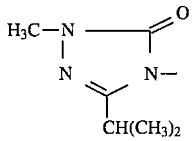 | 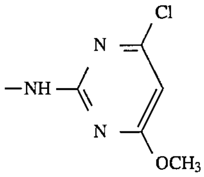 |
| O | 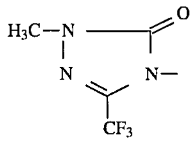 | 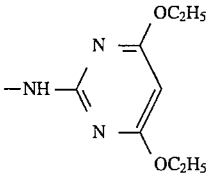 |
TABLE 1-continued
Examples of the compounds of the formula (I)
| Q | $R^1$ | $R^2$ |
|---|---|---|
| O | 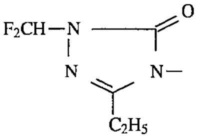 | 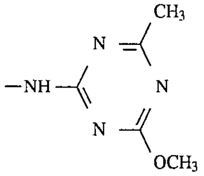 |
| O | 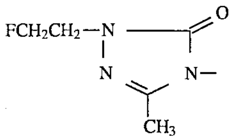 | 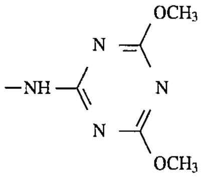 |
| O | 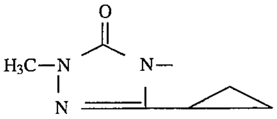 | 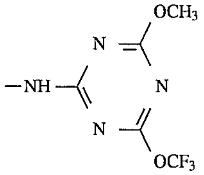 |
| O | 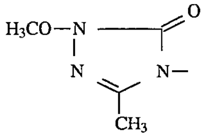 | 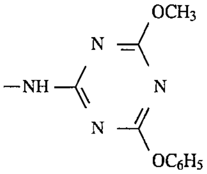 |
| O | 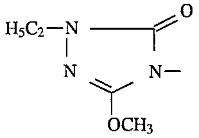 | 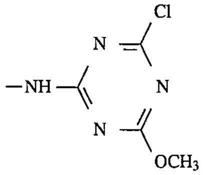 |
| S | 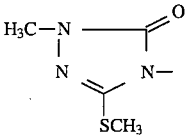 | 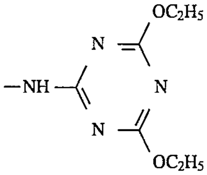 |
| O | 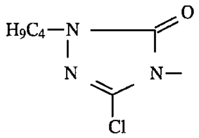 | 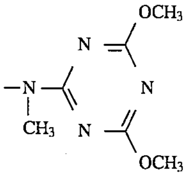 |

TABLE 1-continued
Examples of the compounds of the formula (I)
| Q | $R^1$ | $R^2$ |
| --- | --- | --- |
| O | 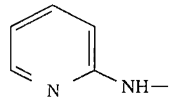 | 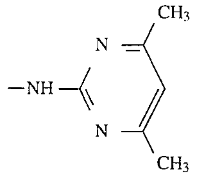 |
| O | 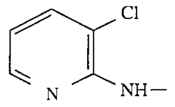 | 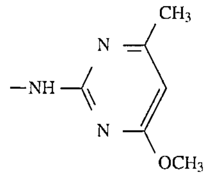 |
| O | 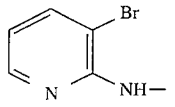 | 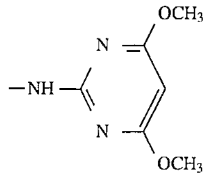 |
| S | 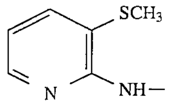 | 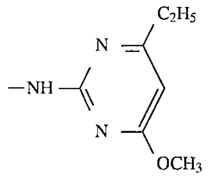 |
| O | 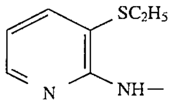 | 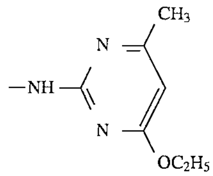 |
| O | 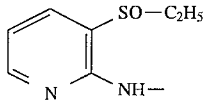 | 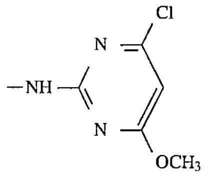 |
| O | 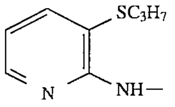 | 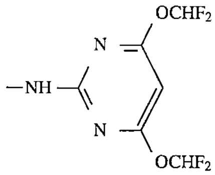 |
| O | 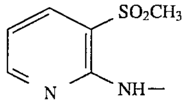 | 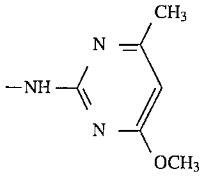 |
TABLE 1-continued
Examples of the compounds of the formula (I)
| Q | $R^1$ | $R^2$ |
| --- | --- | --- |
| O | 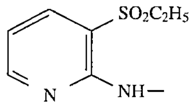 | 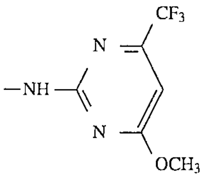 |
| S | 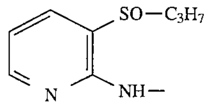 | 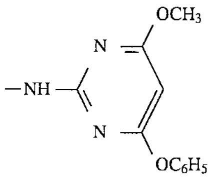 |
| O | 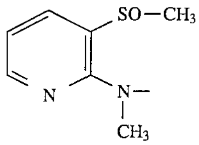 | 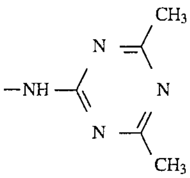 |
| O | 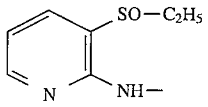 | 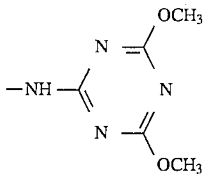 |
| O | 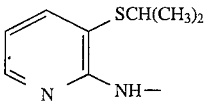 | 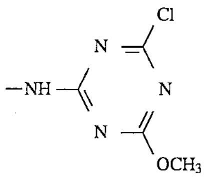 |
| O | 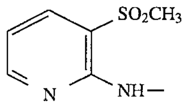 | 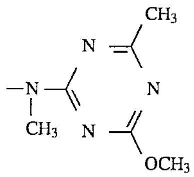 |
| O | 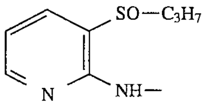 | 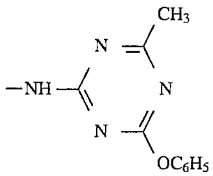 |
| O | 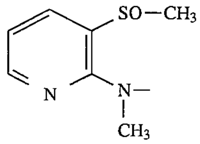 | 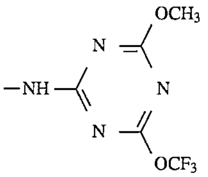 |

TABLE 1-continued
Examples of the compounds of the formula (I)
| Q | $R^1$ | $R^2$ |
|---|---|---|
| O | 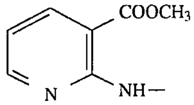 | 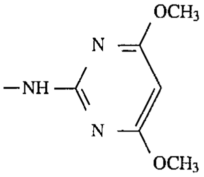 |
| O | 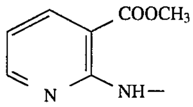 | 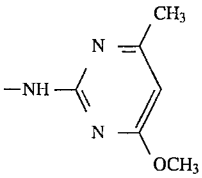 |
| O | 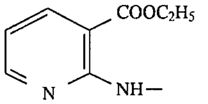 | 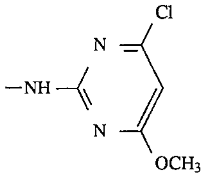 |
| O | 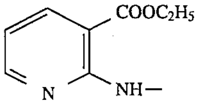 | 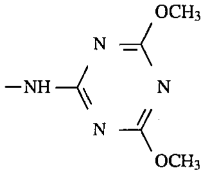 |
| O | 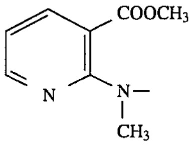 | 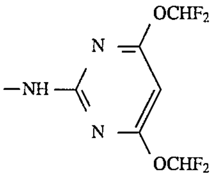 |
| O | 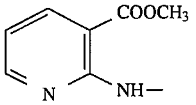 | 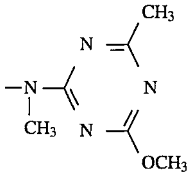 |
| O | 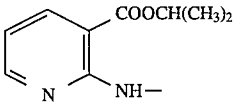 | 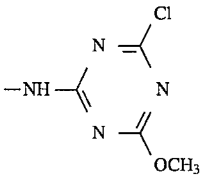 |
| S | 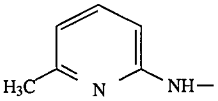 | 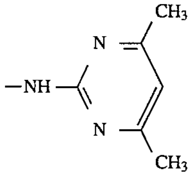 |
| O | 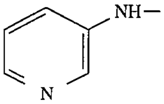 | 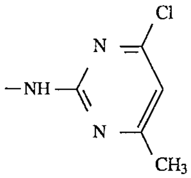 |
| O | 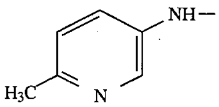 | 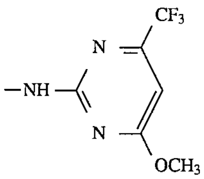 |
| S | 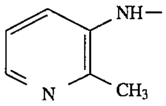 | 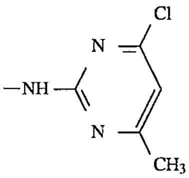 |
| O | 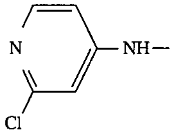 | 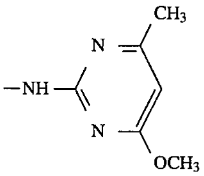 |
| O | 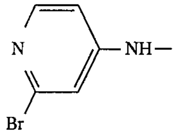 | 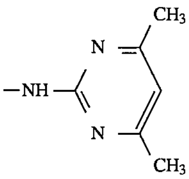 |
| S | 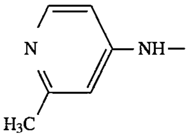 | 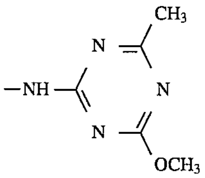 |
| O | 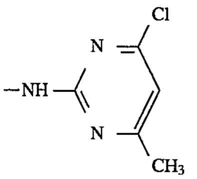 | 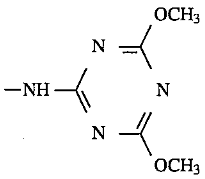 |
| O | 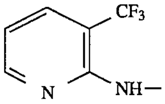 | 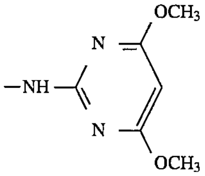 |

TABLE 1-continued
Examples of the compounds of the formula (I)
| Q | $R^1$ | $R^2$ |
|---|---|---|
| O | 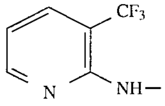 | 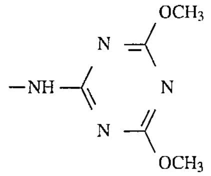 |
| S | 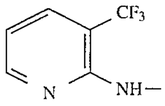 | 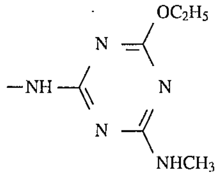 |
| O | 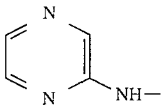 | 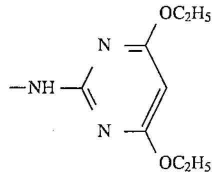 |
| O | 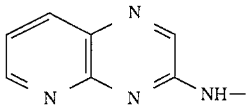 | 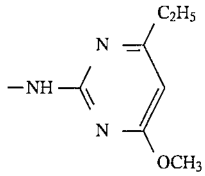 |
| O | 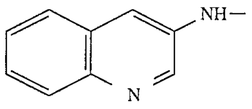 | 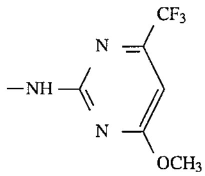 |
| S | 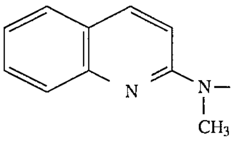 | 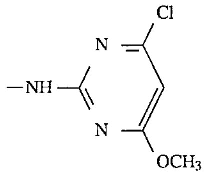 |
| O | 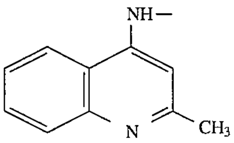 | 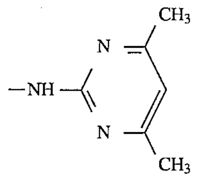 |
| O | 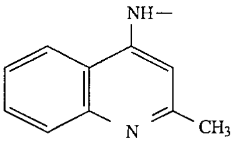 | 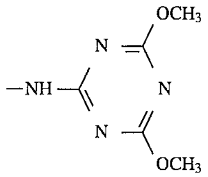 |
TABLE 1-continued
Examples of the compounds of the formula (I)
| Q | $R^1$ | $R^2$ |
|---|---|---|
| O | 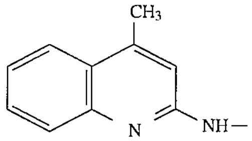 | 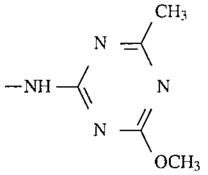 |
| O | 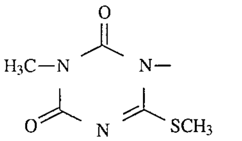 | 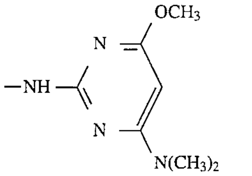 |
| O | 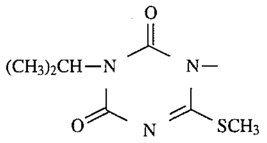 | 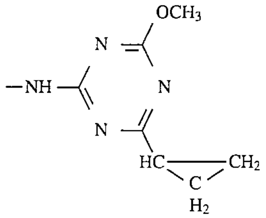 |
| O | 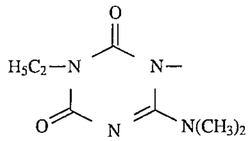 | 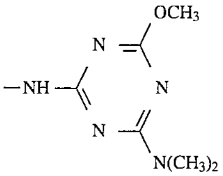 |
| O | 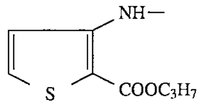 | 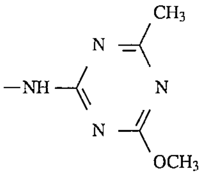 |
| O | 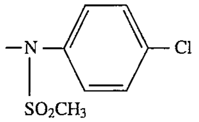 | 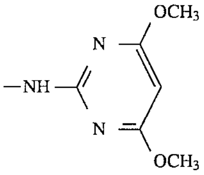 |
| O | 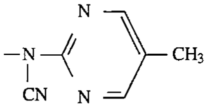 | 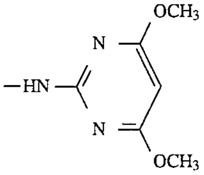 |
| O | 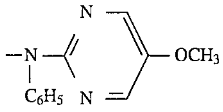 | 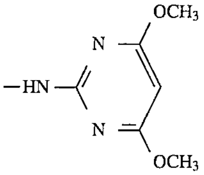 |

TABLE 1-continued

| Examples of the compounds of the formula (I) | | |
|---|---|---|
| Q | $R^1$ | $R^2$ |
| O | 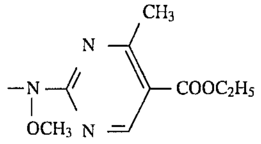 | 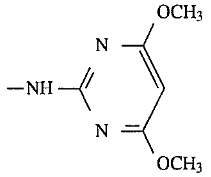 |
| O | 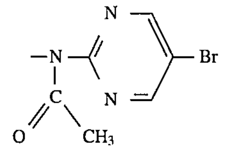 | 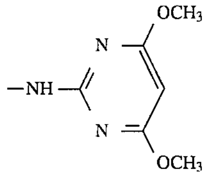 |

If, for example, 3-amino-5-methyl-isoxazol and 5-ethyl-4-methyl-2-phenoxysulphonylaminocarbonyl-2,4-dihydro-3H1,2,4-triazol-3-one are used as starting substances, the course of the reaction in process variant (b) according to the invention can be represented by the following equation:

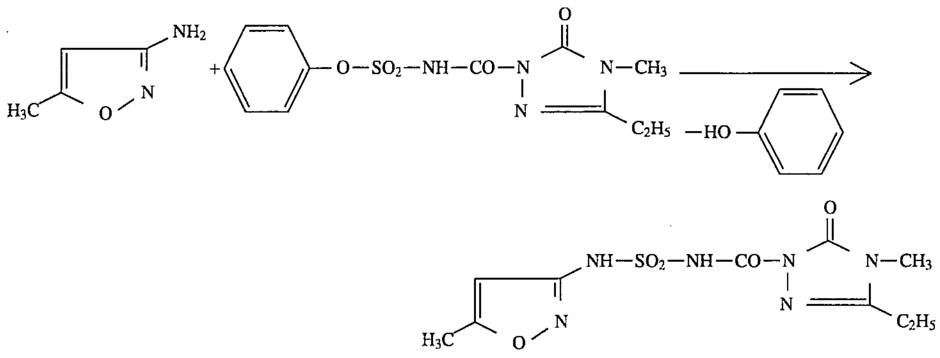

If, for example, 2-amino-4,6-dimethoxy-pyrimidine and chlorosulphonyl isocyanate and, in the consecutive step, 2-methyl-pyrrolidine are used as starting substances, the course of the reaction in process variant (a) according to the invention can be represented by the following equation:

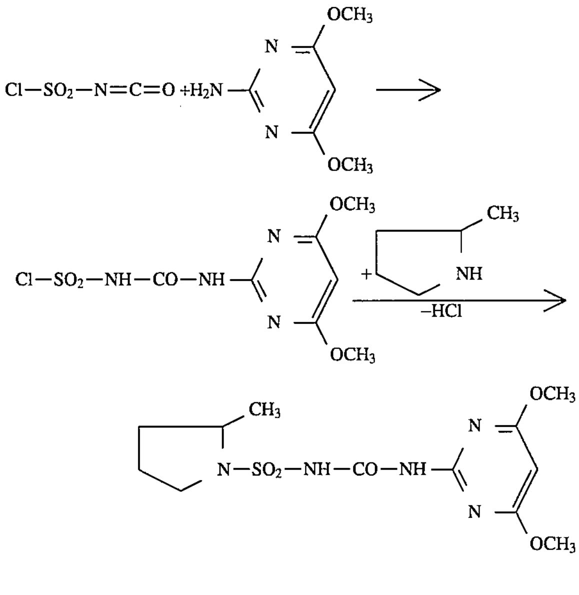

If, for example, 2,3-dihydro-6,8-dimethyl-3-oxo-pyrimidino-[1,2-b]-2,4,6-thiadiazine-1,1-dioxide and2-amino-4,6-dimethoxy-pyrimidine are used as starting substances, the course of the reaction in process variant (c) according to the invention can be represented by the following equation:

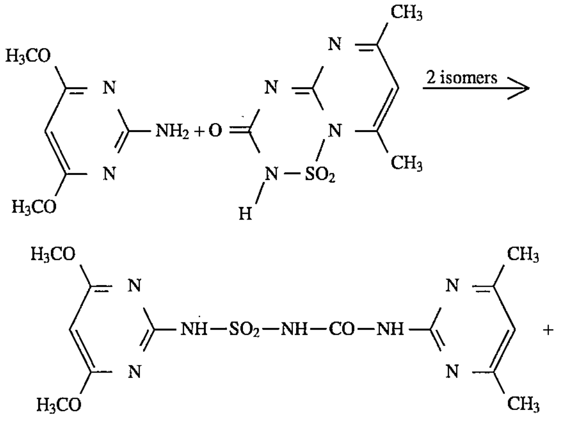

-continued

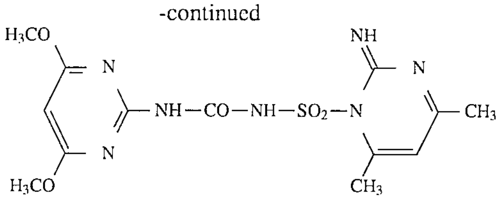

(In general, the two isomers formed in process (c) are isolated separately).

The compounds of the formulae (II), (III) and (V) which are required as starting substances for process (a) according to the invention are known chemicals or can be prepared by processes known per se (cf. EP-A 271833; EP-A 158594; EP-A 424849; EP-A 476554; EP-A 341489; EP-A 422469; EP-A 425948; EP-A 431291; EP-A 477646).

The oxysulphonylamino(thio) carbonyl compounds of the formula (VI) which are required as starting substances for process (b) according to the invention are also known and/or can be prepared by processes known per se (cf. DE-OS (German Published Specification) 3111451).

The azinothiatriazine oxides of the formula (VII) which are required as starting substances for process (c) according to the invention are also known and/or can be prepared by processes known per se (cf. DE-OS (German Published Specification) 3324802).

Processes (a) , (b) and (c) according to the invention for the preparation of the new compounds of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbontetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in processes (a), (b) and (c) according to the invention are all acid-binding agents which can conventionally be used for reactions of this type. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates, such as sodium carbonate, sodium hydrogen carbonate, potassium carbonate or potassium hydrogen carbonate, or calcium carbonate, alkali metal acetates, such as sodium acetate and potassium acetate, alkali metal alcoholates, such as sodium methylate, sodium ethylate, sodium propylate, sodium isopropylate, sodium burylate, sodium isobutylate, sodium tert-butylate, potassium methylate, potassium ethylate, potassium propylate, potassium isopropylate, potassium burylate, potassium isobutylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl- 2-methyl-pyridine, 1,5-diazabicyclo-[4,3,0]-non-5-ene (DBN), 1,8-diazabicyclo-[5,4,0]- undec-7-ene (DBU) and 1,4 -diazabicyclo[2,2,2]-octane (DABCO).

When carrying out processes (a), (b) and (c) according to the invention, the reaction temperatures can be varied within a substantial range. In general, the processes are carried out at temperatures between –70° C. and +100° C., preferably at temperatures between –20° C. and +50° C.

In general, processes (a), (b) and (c) according to the invention are carried out under atmospheric pressure. However, they can also be carried out under elevated or reduced pressure.

To carry out processes (a), (b) and (c) according to the invention, the starting substances required in each case are generally employed in approximate equimolar amounts. However, it is also possible to use one of the components employed in each case in a larger excess. In general, the reactions are carried out in a suitable diluent in the presence of an acid acceptor, and the reaction mixture is stirred for several hours at the temperature required in each case. Working-up in the process according to the invention is carried out in each case by customary methods.

If appropriate, salts can be prepared with the compounds of the general formula (I) according to the invention. Such salts are obtained in a simple manner by customary salt formation methods, for example by dissolving or dispersing a compound of the formula (I) in a suitable diluent, such as, for example, methylene chloride, acetone, tert-butyl methyl ether or toluene, and adding a suitable base. The salts can then be isolated by concentration or filtration with suction, if appropriate after prolonged stirring (cf. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants Dicotyledon weeds of the general Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the general

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the general

Echinochloa, Setaria, Panicum, Digitaria, Phleum, Poa, Festuca, Eleusine, Brachiaria, Lolium, Bromus, Arena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the general

Oryza, Zea, Triticum, Hordeum, Arena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land and for the selective combating of weeds in annual cultures.

The compounds of the formula (I) according to the invention are particularly suitable for selectively combating dicotyledon weeds in monoctyledon cultures, such as, for example, in cereals, especially by the post-emergence method.

The active compounds can be converted into the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example by mixing the active compounds with extenders that is, liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxapropethyl, fluazifop-butyl, haloxyfopmethyl and quizalofopethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amido-sulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and the use of the compounds according to the invention can be seen from the examples which follow.

PREPARATION EXAMPLES:

Example 1

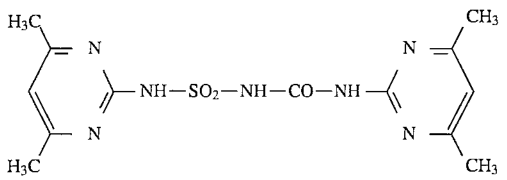

(Process (a))

7.1 g (0.05 mol) of chlorosulphonyl isocyanate are added dropwise with stirring at 22° C. to a solution of 6.2 g (0.05 mol) of 2-amino-4,6-dimethyl-pyrimidine and 5.0 g (0.055 mol) of triethylamine in 200 ml of methylene chloride, and the mixture is stirred for a further 30 minutes at 22° C. Another 6.2 g (0.05 mol) of 2-amino-4,6-dimethyl-pyrimidine are then added, and the mixture is stirred for 18 hours at 22° C. It is then subjected to filtration with suction, the filter cake is stirred with 200 ml of water, and the undissolved product is isolated by filtration with suction.

8.4 g (48% of theory) of 1-(4,6-dimethyl-pyrimidine-2-yl)-3-(4,6-dimethyl-pyrimidine-2-yl-amino-sulphonyl)-urea of melting point 198° C. are obtained.

Example 2

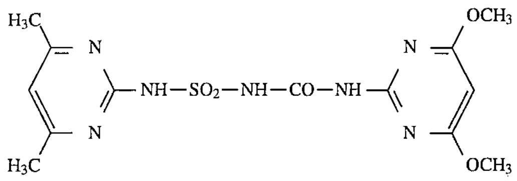

(Process (a))

7.1 g (0.05 mol) of chlorosulphonyl isocyanate are added dropwise with stirring at 0° C. to 5° C. to a solution of 7.7 g (0.05 mol) of 2-amino-4,6-dimethoxy-pyrimidine in 150 ml of methylene chloride, and the mixture is stirred for 30 minutes at 0° C. to 5° C. A solution of 6.2 g (0.05 mol) of 2-amino-4,6-dimethyl-pyrimidine and 5.5 g (0.055 mol) of triethylamine in 100 ml of methylene chloride is then added dropwise with stirring, and the mixture is stirred for a further 18 hours at 22° C. It is subsequently concentrated, the residue is stirred with 80 ml of ethanol, and the crystalline product is isolated by filtration with suction.

10.2 g (53% of theory) of 1-(4,6-dimethoxy-pyrimidine-2yl)-3-(4,6-dimethyl-pyrimidine-2-yl-amino-suphonyl)-urea of melting point 254° C. are obtained.

Example 3

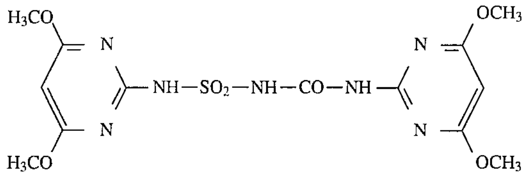

(Process (a))

7.1 g (0.05 mol) of chlorosulphonyl isocyanate are added dropwise with stirring at 22° C. to a mixture of 15.5 g (0.10 mol) of 2-amino-4,6-dimethoxy-pyrimidine, 5.5 g (0.055 mol) of triethylamine and 200 ml of methylene chloride. The reaction mixture is stirred for 18 hours at 22° C. and then concentrated. The residue is then stirred with 70 ml of water, and the crystalline product is isolated by filtration with suction.

12.6 g (60% of theory) of 1-(4,6-dimethoxy-pyrimidine-2-yl)-3-(4,6-dimethoxy-pyrimidine-2-yl-amino-sulphonyl)-urea of melting point 210° C. are obtained.

Example 4

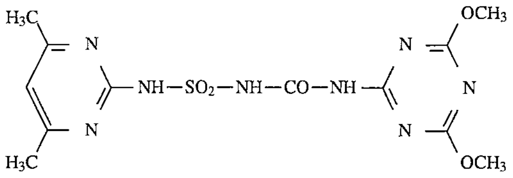

(Process (c))

6.2 g (0.05 mol) of 2-amino-4,6-dimethyl-pyrimidine are added in portions with stirring to a mixture of 14.9 g (0.05 mol) of 2,3-dihydro-6,8-dimethoxy-3-oxo-s-triazino[1,2-b]-1,2,4,6-thiatriazine 1,1-dioxide (disclosed in DE-OS (German Published Specification) 3 324 802) and 150 ml of methylene chloride, the temperature not being allowed to exceed 35° C. 5.5 g (0.055 mol) of triethylamine are subsequently added dropwise, and the reaction mixture is then stirred for 18 hours at 20° C. It is subsequently filtered, the filtrate is evaporated, and the residue is triturated with ethanol. The product obtained in this process in the form of crystals is isolated by filtration with suction.

7.0 g (36.5% of theory) of 1-(4,6-dimethoxy-s-triazine-2-yl)-3-(4,6-dimethyl-pyrimidine-2-yl-amino-sulphonyl)-urea of melting point 172° C. are obtained.

Other examples of compounds of the formula (I) which can be prepared analogously to Preparation Examples 1 to 4 and following the general description of the processes according to the invention are those mentioned in Table 2 below.

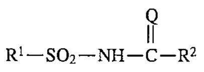

(I)

TABLE 2
Examples of the compounds of the formula (I)
| Ex. No. | Q | $R^1$ | $R^2$ | Melting point (°C.) |
|---|---|---|---|---|
| 5 | O | 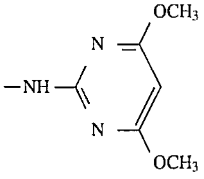 | 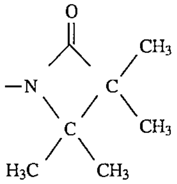 | 133 |
| 6 | O | 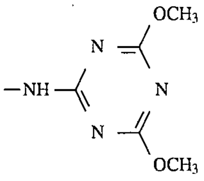 | 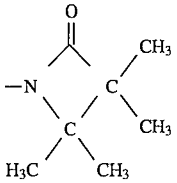 | 156 |
| 7 | O | 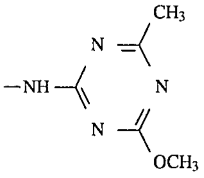 | 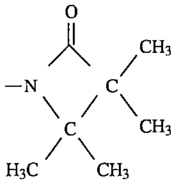 | 158 |
| 8 | O | 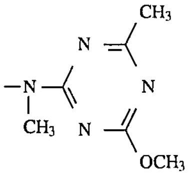 | 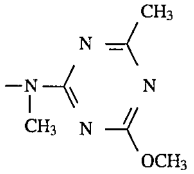 | |
| 9 | O | 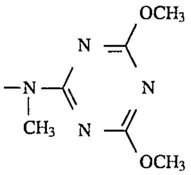 | 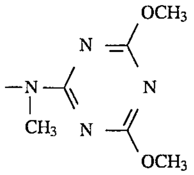 | 165 |
| 10 | O | 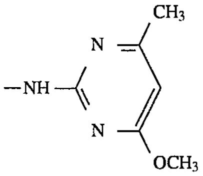 | 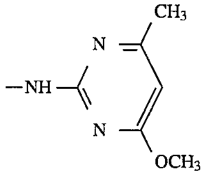 | 143 |
| 11 | O | 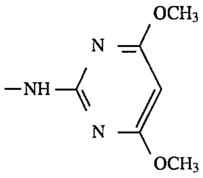 | 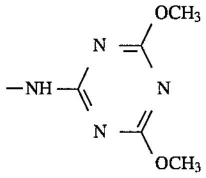 | 265 |
| 12 | O | 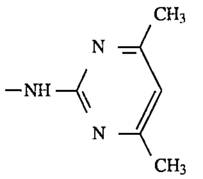 | 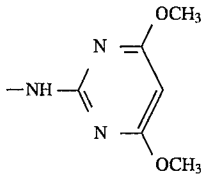 | 202 |

TABLE 2-continued
| Examples of the compounds of the formula (I) | | | | |
|---|---|---|---|---|
| Ex. No. | Q | $R^1$ | $R^2$ | Melting point (°C.) |
| 13 | O | 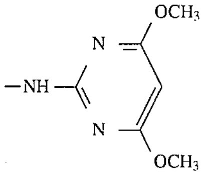 | 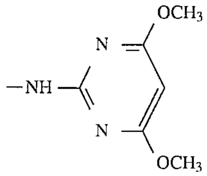 | 246 |
| 14 | O | 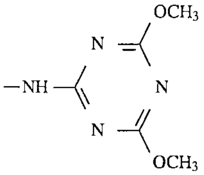 | 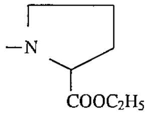 | 174 |
| 15 | O | 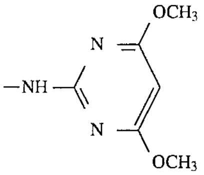 | 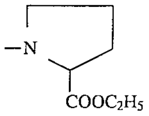 | 144 |
| 16 | O | 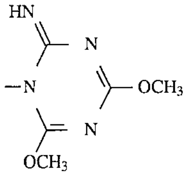 | 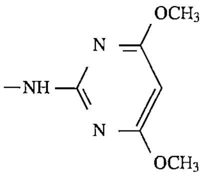 | 185 |
| 17 | O | 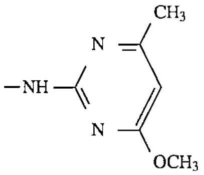 | 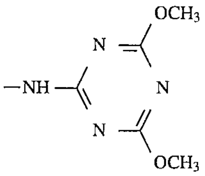 | 210 |
| 18 | O | 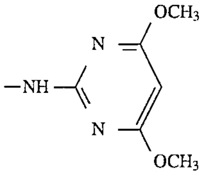 | 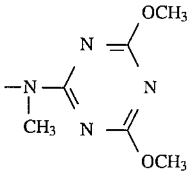 | 192 |
| 19 | O | 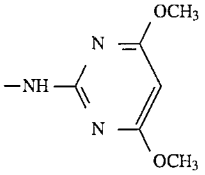 | 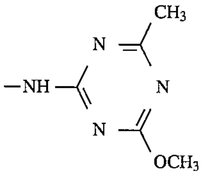 | 188 |
| 20 | O | 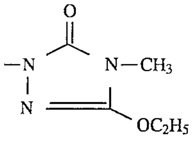 | 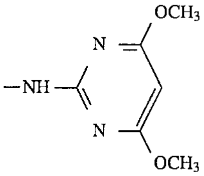 | 200 |

TABLE 2-continued
Examples of the compounds of the formula (I)
| Ex. No. | Q | $R^1$ | $R^2$ | Melting point (°C.) |
|---|---|---|---|---|
| 21 | O | 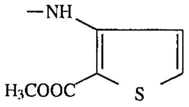 | 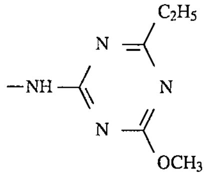 | |
| 22 | O | 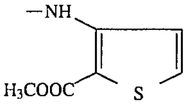 | 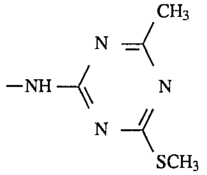 | |
| 23 | O | 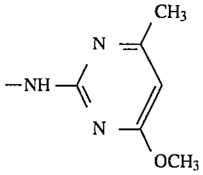 | 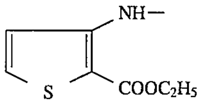 | |
| 24 | O | 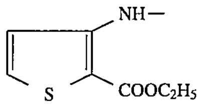 | 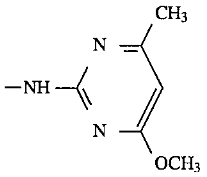 | |
| 25 | O | 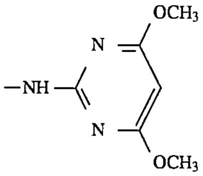 | 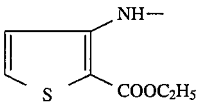 | |
| 26 | O | 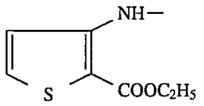 | 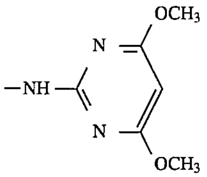 | |
| 27 | O | 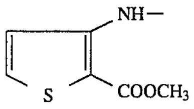 | 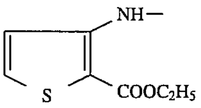 | |
| 28 | O | 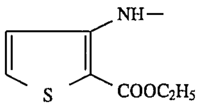 | 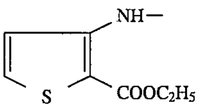 | |
| 29 | O | 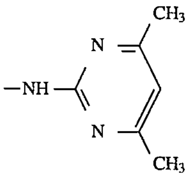 | 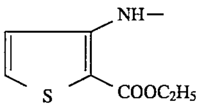 | |

TABLE 2-continued
Examples of the compounds of the formula (I)
| Ex. No. | Q | $R^1$ | $R^2$ | Melting point (°C.) |
|---|---|---|---|---|
| 30 | O | 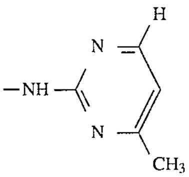 | 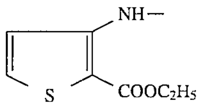 | |
| 31 | O | 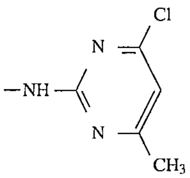 | 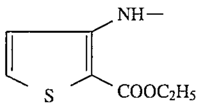 | |
| 32 | O | 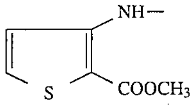 | 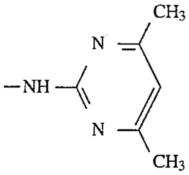 | |
| 33 | O | 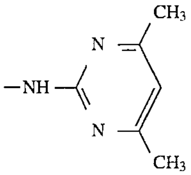 | 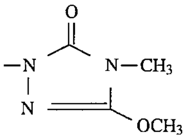 | |
| 34 | O | 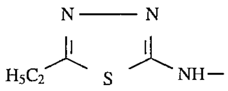 | 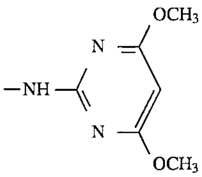 | 177 |
| 35 | O | 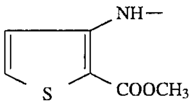 | 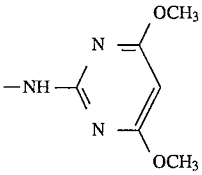 | 151 |
| 36 | O | 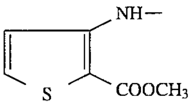 | 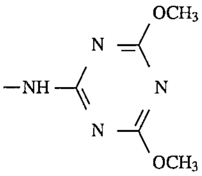 | 154 |
| 37 | O | 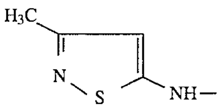 | 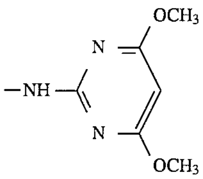 | 146 |

TABLE 2-continued
Examples of the compounds of the formula (I)
| Ex. No. | Q | $R^1$ | $R^2$ | Melting point (°C.) |
|---|---|---|---|---|
| 38 | O | 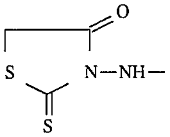 | 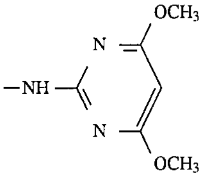 | 162 |
| 39 | O | 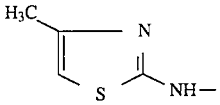 | 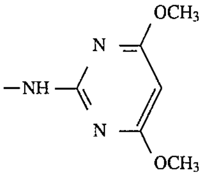 | 200 |
| 40 | O | 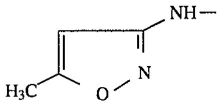 | 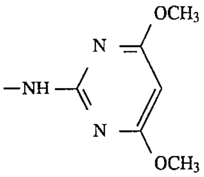 | 148 |
| 41 | O | 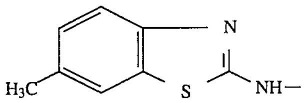 | 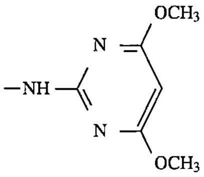 | 186 |
| 42 | O | 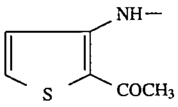 | 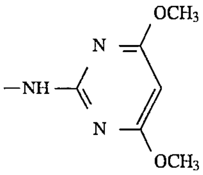 | 162 |
| 43 | O | 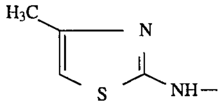 | 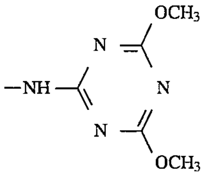 | 189 |
| 44 | O | 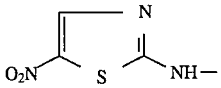 | 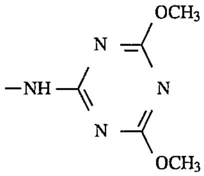 | >250 |
| 45 | O | 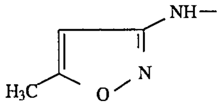 | 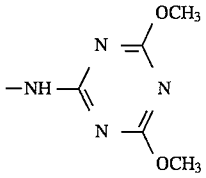 | 152 |

TABLE 2-continued
Examples of the compounds of the formula (I)
| Ex. No. | Q | $R^1$ | $R^2$ | Melting point (°C.) |
| --- | --- | --- | --- | --- |
| 46 | O | 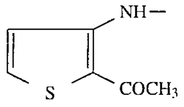 | 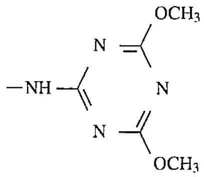 | 169 |
| 47 | O | 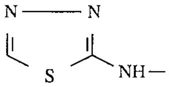 | 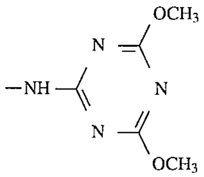 | 280 |
| 48 | O | 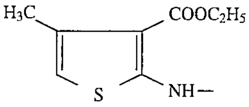 | 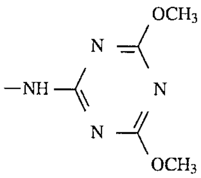 | 146 |
| 49 | O | 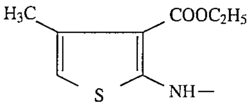 | 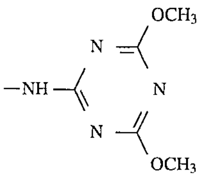 | 160 |
| 50 | O | 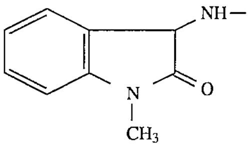 | 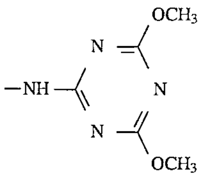 | 175 |
| 51 | O | 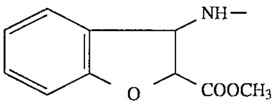 | 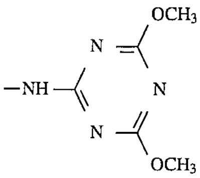 | 175 |
| 52 | O | 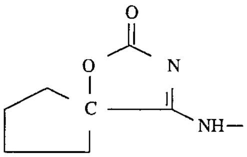 | 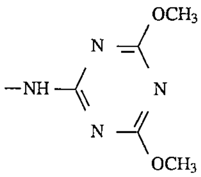 | 225 |
| 53 | O | 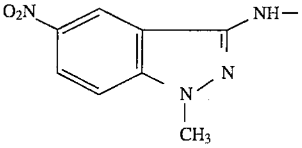 | 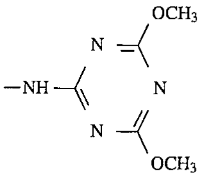 | 205 |

TABLE 2-continued
Examples of the compounds of the formula (I)
| Ex. No. | Q | $R^1$ | $R^2$ | Melting point (°C.) |
|---|---|---|---|---|
| 54 | O | 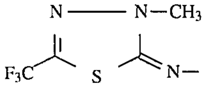 | 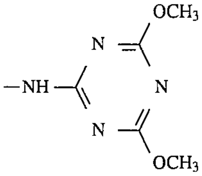 | 184 |
| 55 | O | 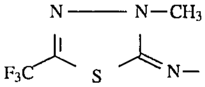 | 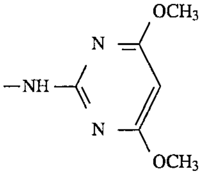 | 174 |
| 56 | O | 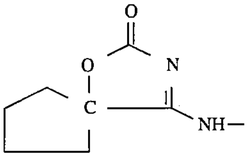 | 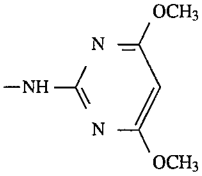 | 185 |
| 57 | O | 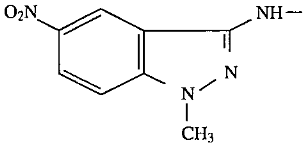 | 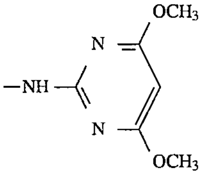 | 231 |
| 58 | O | 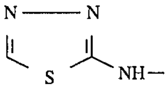 | 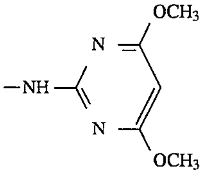 | 186 |
| 59 | O | 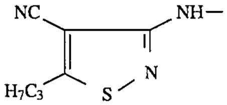 | 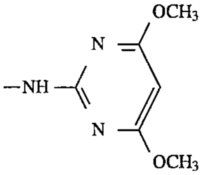 | 150 |
| 60 | O | 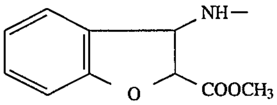 | 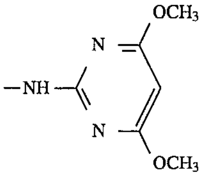 | 161 |
| 61 | O | 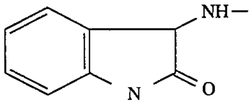 | 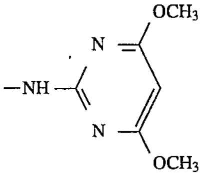 | 163 |

TABLE 2-continued
Examples of the compounds of the formula (I)
| Ex. No. | Q | $R^1$ | $R^2$ | Melting point (°C.) |
|---|---|---|---|---|
| 62 | O | 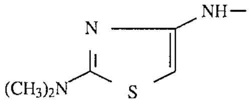 | 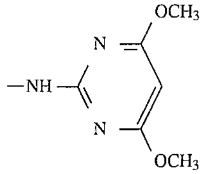 | 168 |
| 63 | O | 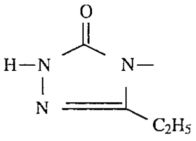 | 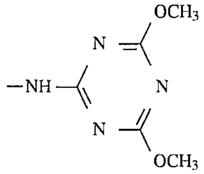 | 135 |
| 64 | O | 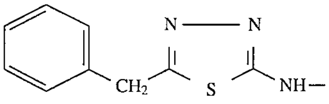 | 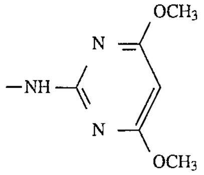 | 170 |
| 65 | O | 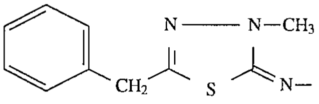 | 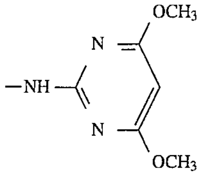 | 186 |
| 66 | O | 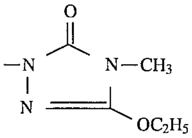 | 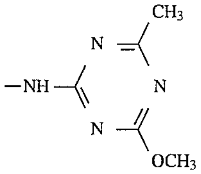 | 195 |
| 67 | O | 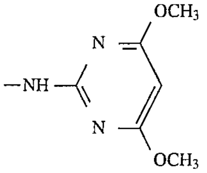 | 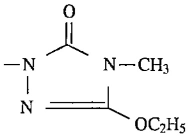 | 88 |
| 68 | O | 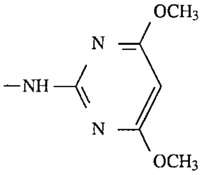 | 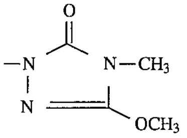 | 148 |
| 69 | O | 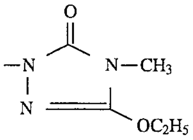 | 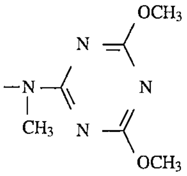 | 140*) |

TABLE 2-continued
Examples of the compounds of the formula (I)
| Ex. No. | Q | $R^1$ | $R^2$ | Melting point (°C.) |
|---|---|---|---|---|
| 70 | O | 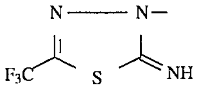 | 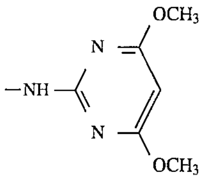 | 188 |
| 71 | O | 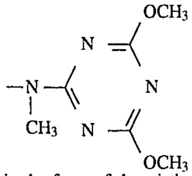 | 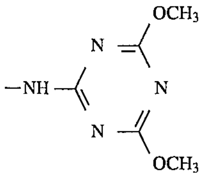 | |
| *) obtained in the form of the triethylammonium salt | | | | |
| 72 | O | 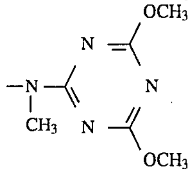 | 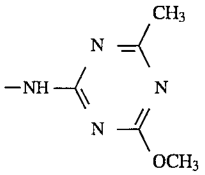 | 162 |
| 73 | O | 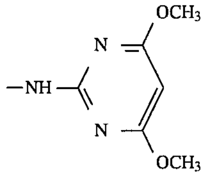 | 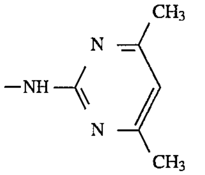 | 270 |
| 74 | O | 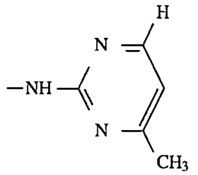 | 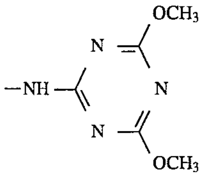 | 222 |
| 75 | O | 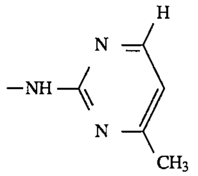 | 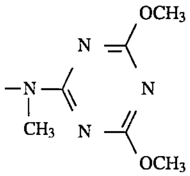 | >300 |
| 76 | O | 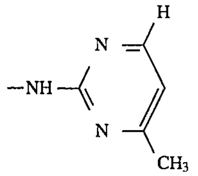 | 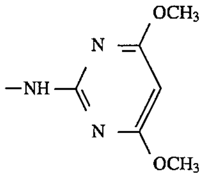 | 196 |
| 77 | O | 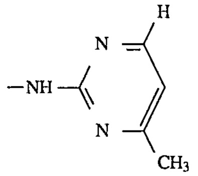 | 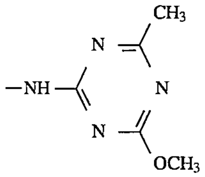 | 214 |

TABLE 2-continued
| Ex. No. | Q | R[1] | R[2] | Melting point (°C.) |
| --- | --- | --- | --- | --- |
| | | Examples of the compounds of the formula (I) | | |
| 78 | O | 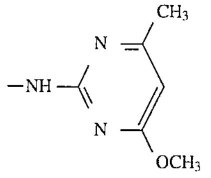 | 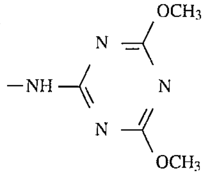 | 108 |
| 79 | O | 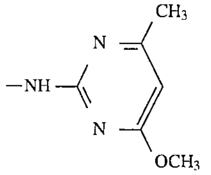 | 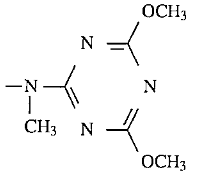 | 192 |
| 80 | O | 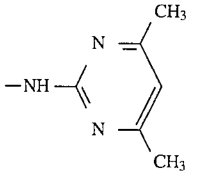 | 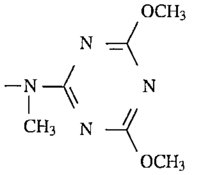 | 186 |
| 81 | O | 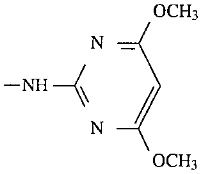 | 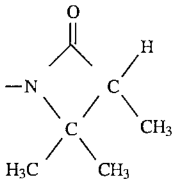 | 145 |
| 82 | O | 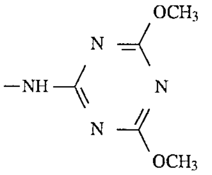 | 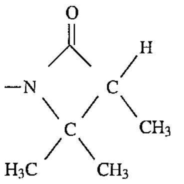 | 138 |
| 83 | O | 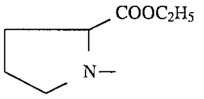 | 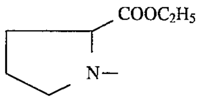 | (oil) |
| 84 | O | 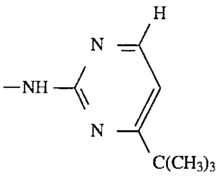 | 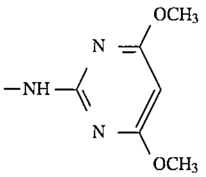 | 140 |
| 85 | O | 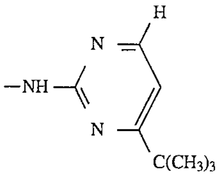 | 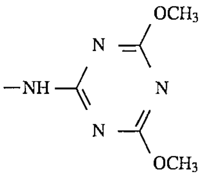 | 172 |

TABLE 2-continued
Examples of the compounds of the formula (I)
| Ex. No. | Q | $R^1$ | $R^2$ | Melting point (°C.) |
|---|---|---|---|---|
| 86 | O | 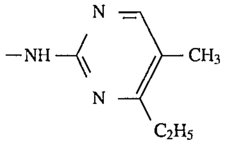 | 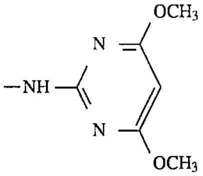 | 180 |
| 87 | O | 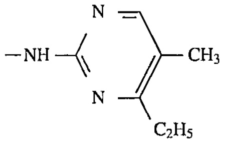 | 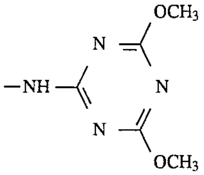 | 205 |
| 88 | O | 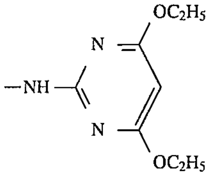 | 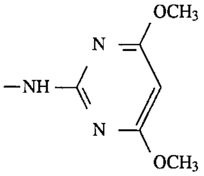 | 182 |
| 89 | O | 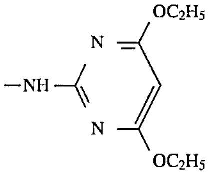 | 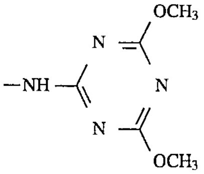 | 145 |
| 90 | O | 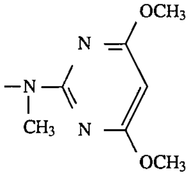 | 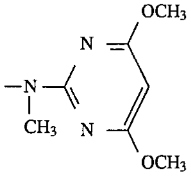 | 162 |
| 91 | O | 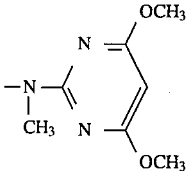 | 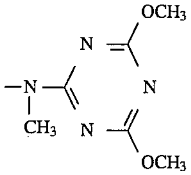 | 137 |
| 92 | O | 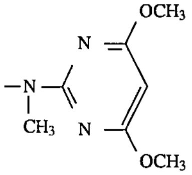 | 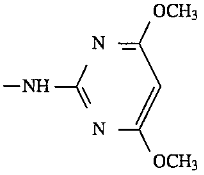 | 144 |
| 93 | O | 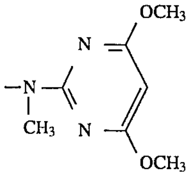 | 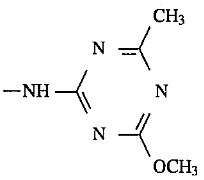 | 148 |

TABLE 2-continued
Examples of the compounds of the formula (I)
| Ex. No. | Q | $R^1$ | $R^2$ | Melting point (°C.) |
|---|---|---|---|---|
| 94 | O | 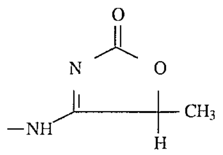 | 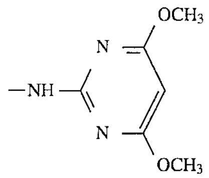 | 190 |
| 95 | O | 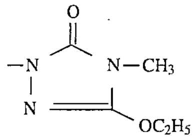 | 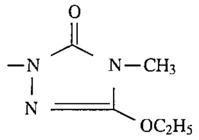 | (amorphous)*) |
| 96 | O | 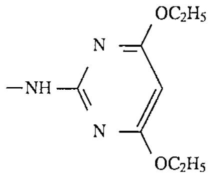 | 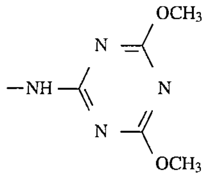 | 130 |
| 97 | O | 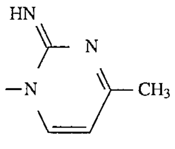 | 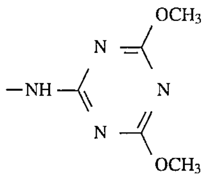 | |
| 98 | O | 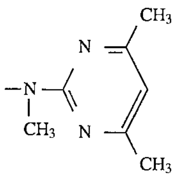 | 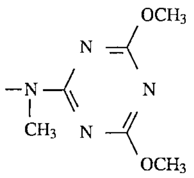 | 152 |
*)obtained in the form of the triethylammonium salt
| | | | | |
|---|---|---|---|---|
| 99 | O | 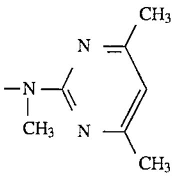 | 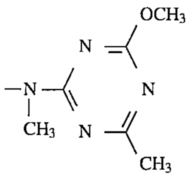 | 154 |
| 100 | O | 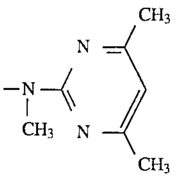 | 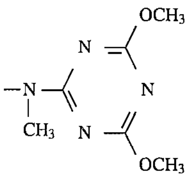 | 152 |
| 101 | O | 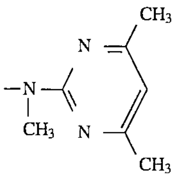 | 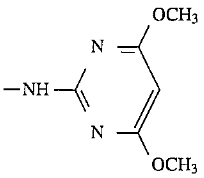 | 168 |

TABLE 2-continued
Examples of the compounds of the formula (I)
| Ex. No. | Q | $R^1$ | $R^2$ | Melting point (°C.) |
|---|---|---|---|---|
| 102 | O | 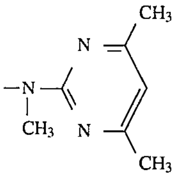 | 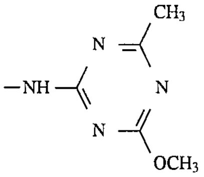 | 162 |
| 103 | O | 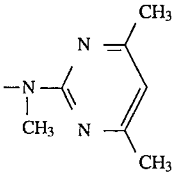 | 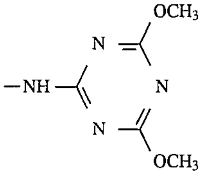 | 164 |
| 104 | O | 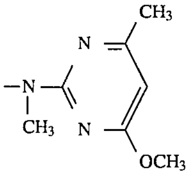 | 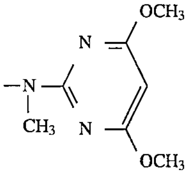 | 162 |
| 105 | O | 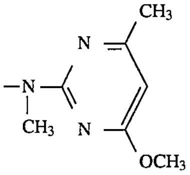 | 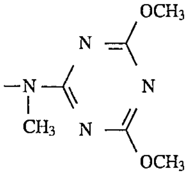 | 132 |
| 106 | O | 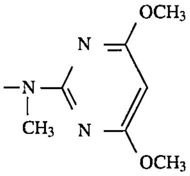 | 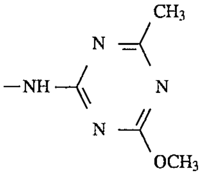 | 140 |
| 107 | O | 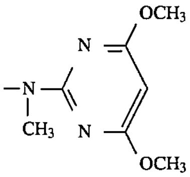 | 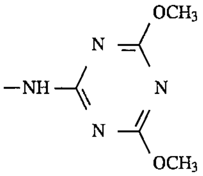 | 182 |
| 108 | O | 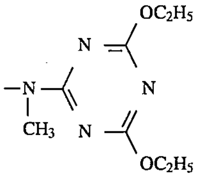 | 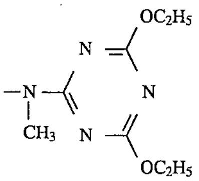 | 123 |
| 109 | O | 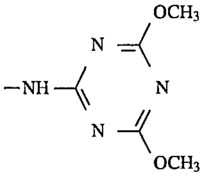 | 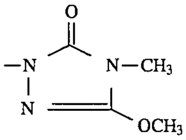 | 158 |

TABLE 2-continued
Examples of the compounds of the formula (I)
| Ex. No. | Q | $R^1$ | $R^2$ | Melting point (°C.) |
|---|---|---|---|---|
| 110 | O | 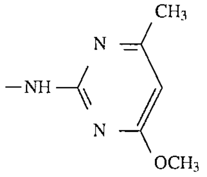 | 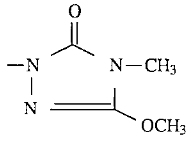 | 165 |
| 111 | O | 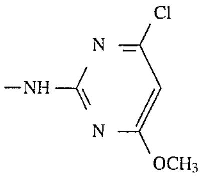 | 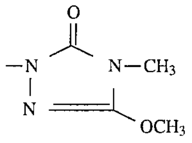 | 160 |
| 112 | O | 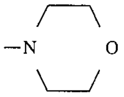 | 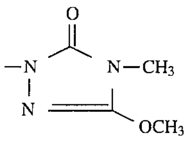 | 204 |
| 113 | O | 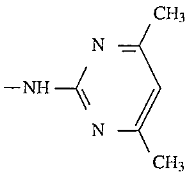 | 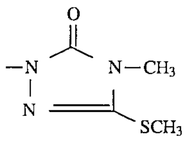 | 147 |
| 114 | O | 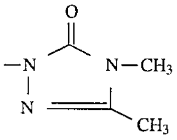 | 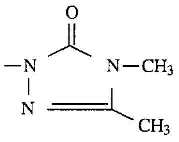 | 140 (obtained in the form of the triethyl-ammonium salt) |
| 115 | O | 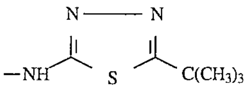 | 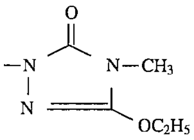 | 160 |
| 116 | O | 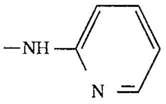 | 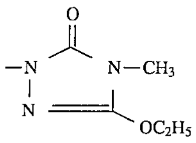 | 172 |
| 117 | O | 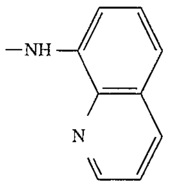 | 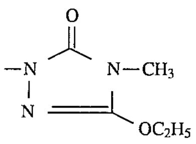 | 135 |
| 118 | O | 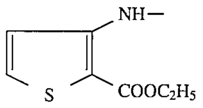 | 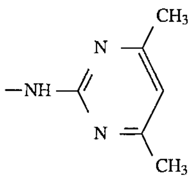 | 140 |

TABLE 2-continued
| Ex. No. | Q | R[1] | R[2] | Melting point (°C.) |
|---|---|---|---|---|
| | | Examples of the compounds of the formula (I) | | |
| 119 | O | 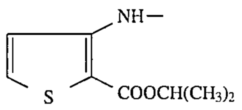 | 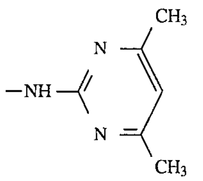 | 112 |
| 120 | O | 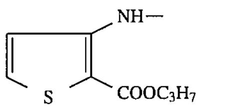 | 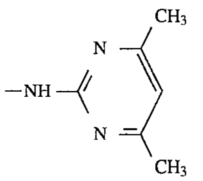 | 200 |
| 121 | O | 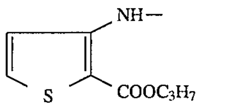 | 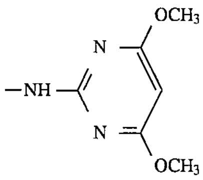 | 172 |
| 122 | O | 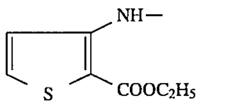 | 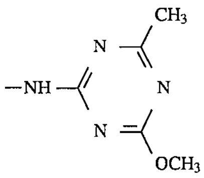 | 147 |
| 123 | O | 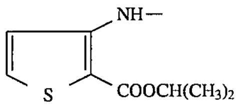 | 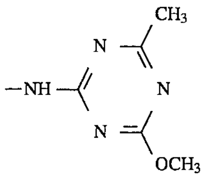 | 183 |
| 124 | O | 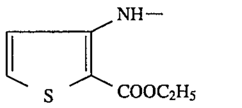 | 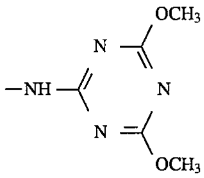 | 149 |
| 125 | O | 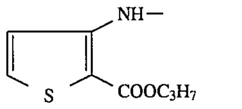 | 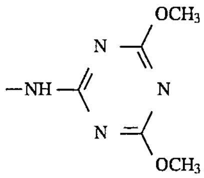 | 151 |
| 126 | O | 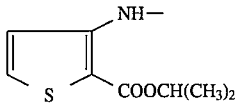 | 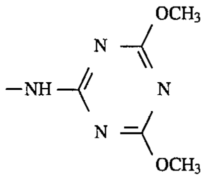 | 156 |

TABLE 2-continued
Examples of the compounds of the formula (I)
| Ex. No. | Q | $R^1$ | $R^2$ | Melting point (°C.) |
|---|---|---|---|---|
| 127 | O | 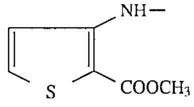 | 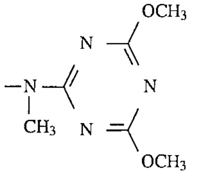 | 132 |
| 128 | O | 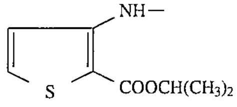 | 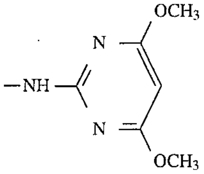 | 184 |
| 129 | O | 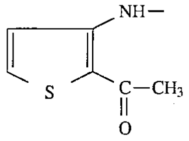 | 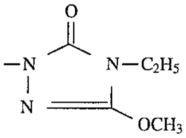 | 154 |
| 130 | O | 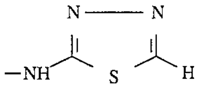 | 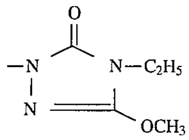 | 181 |
| 131 | O | 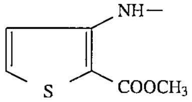 | 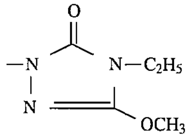 | 176 |
| 132 | O | 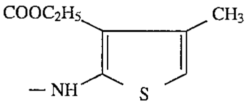 | 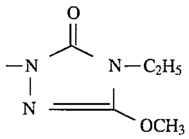 | 136 |
| 133 | O | 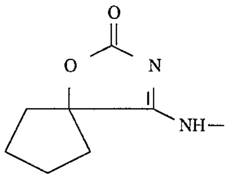 | 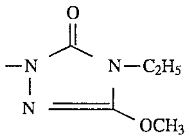 | 180 |
| 134 | O | 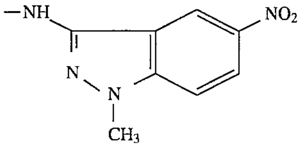 | 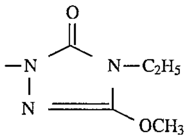 | 248 |
| 135 | O | 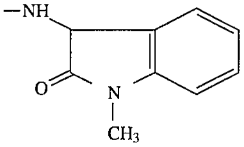 | 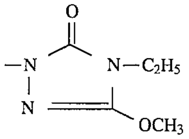 | 159 |

TABLE 2-continued
Examples of the compounds of the formula (I)
| Ex. No. | Q | $R^1$ | $R^2$ | Melting point (°C.) |
|---|---|---|---|---|
| 136 | O | 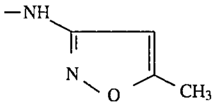 | 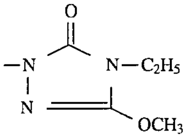 | 145 |
| 137 | O | 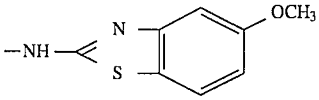 | 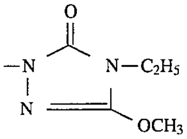 | 190 |
| 138 | O | 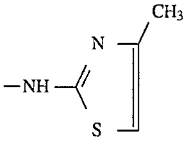 | 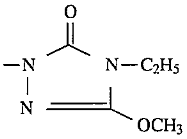 | 171 |
| 139 | O | 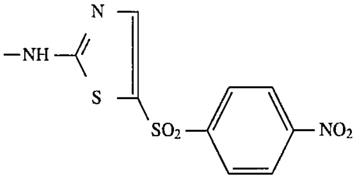 | 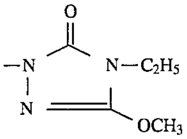 | 166 |
| 140 | O | 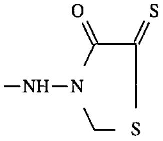 | 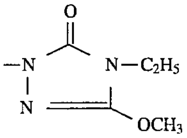 | 155 |
| 141 | O | 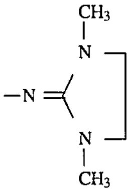 | 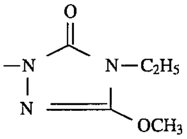 | 176 |
| 142 | O | 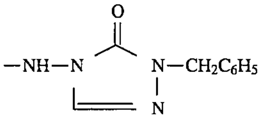 | 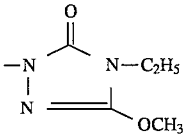 | 167 |
| 143 | O | 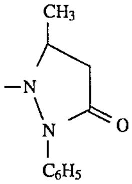 | 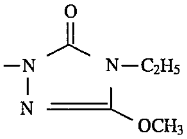 | 133 |
| 144 | O | 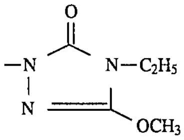 | 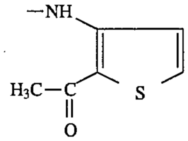 | 85 |

TABLE 2-continued
Examples of the compounds of the formula (I)
| Ex. No. | Q | $R^1$ | $R^2$ | Melting point (°C.) |
|---|---|---|---|---|
| 145 | O | 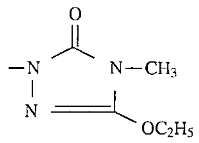 | 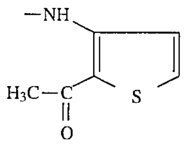 | 122 |
| 146 | O | 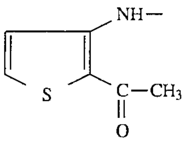 | 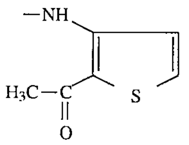 | 157 |
| 147 | O | 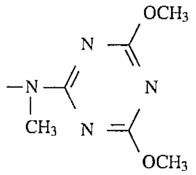 | 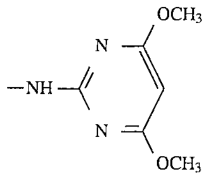 | 205 |
| 148 | O | 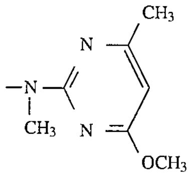 | 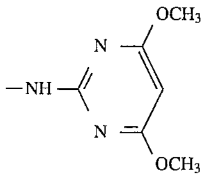 | 218 |
| 149 | O | 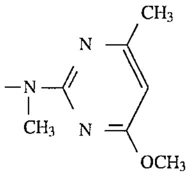 | 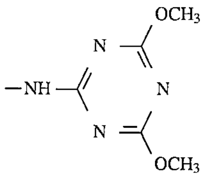 | 158 |
| 150 | O | 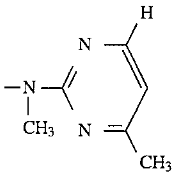 | 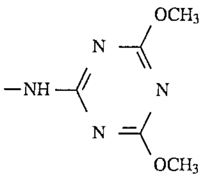 | 150 |
| 151 | O | 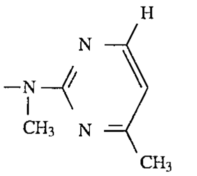 | 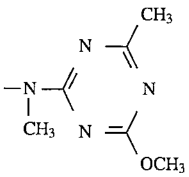 | 123 |
| 152 | O | 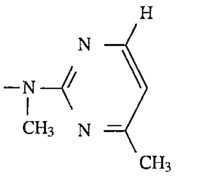 | 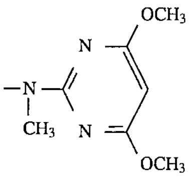 | 132 |

TABLE 2-continued
Examples of the compounds of the formula (I)
| Ex. No. | Q | $R^1$ | $R^2$ | Melting point (°C.) |
|---|---|---|---|---|
| 153 | O | 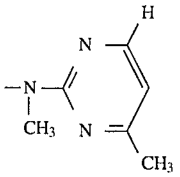 | 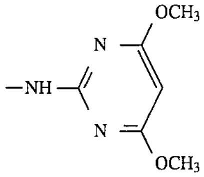 | 158 |
| 154 | O | 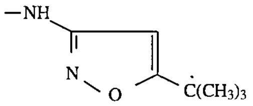 | 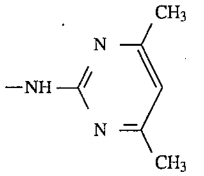 | 186 |
| 155 | O | 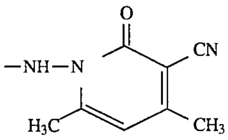 | 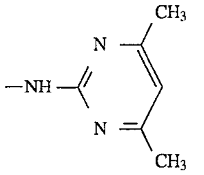 | 218 |
| 156 | O | 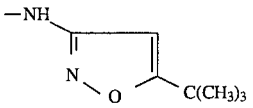 | 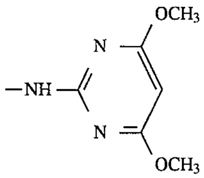 | 216 |
| 157 | O | 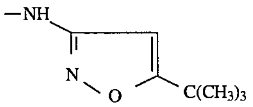 | 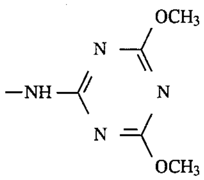 | 190 |
| 158 | O | 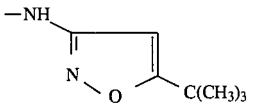 | 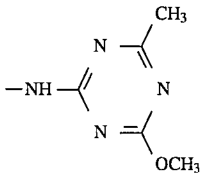 | 174 |
| 159 | O | 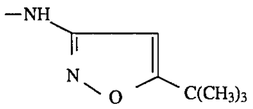 | 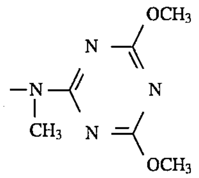 | 141 |
| 160 | O | 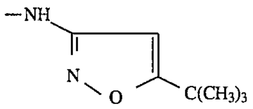 | 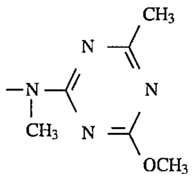 | 155 |

TABLE 2-continued
Examples of the compounds of the formula (I)
| Ex. No. | Q | $R^1$ | $R^2$ | Melting point (°C.) |
|---|---|---|---|---|
| 161 | O | 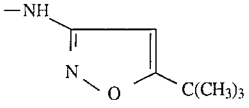 | 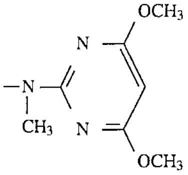 | 160 |
| 162 | O | 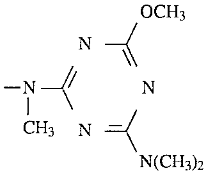 | 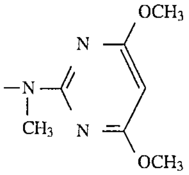 | 134 |
| 163 | O | 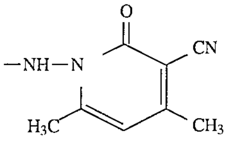 | 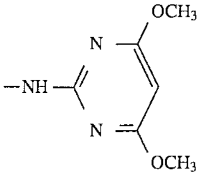 | 226 |
| 164 | O | 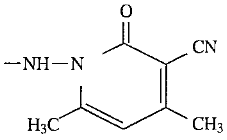 | 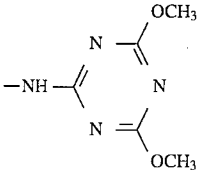 | 166 |
| 165 | O | 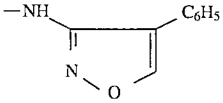 | 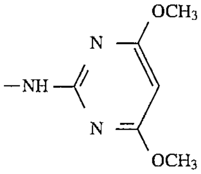 | 188 |
| 166 | O | 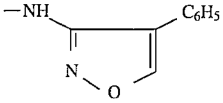 | 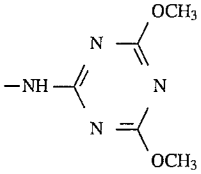 | 184 |
| 167 | O | 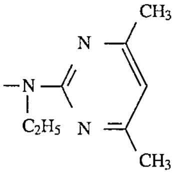 | 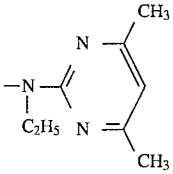 | 175 |
| 168 | O | 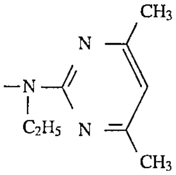 | 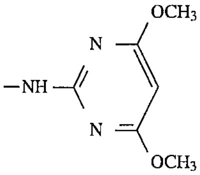 | 192 |

TABLE 2-continued
Examples of the compounds of the formula (I)
| Ex. No. | Q | $R^1$ | $R^2$ | Melting point (°C.) |
|---|---|---|---|---|
| 169 | O | 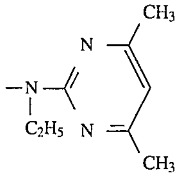 | 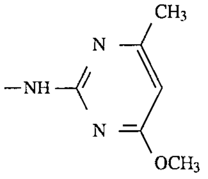 | 198 |
| 170 | O | 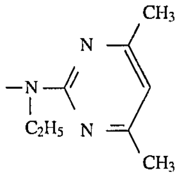 | 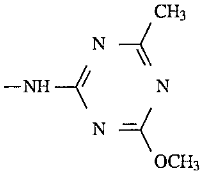 | 174 |
| 171 | O | 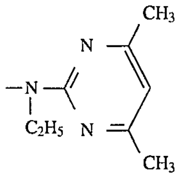 | 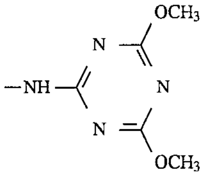 | 186 |
| 172 | O | 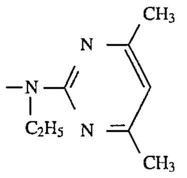 | 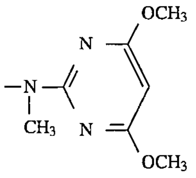 | 168 |
| 173 | O | 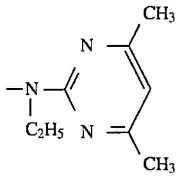 | 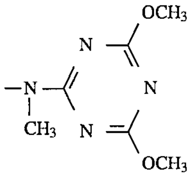 | 161 |
| 174 | O | 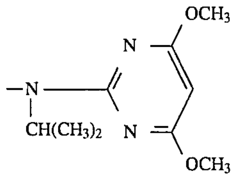 | 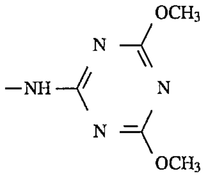 | 185 |
| 175 | O | 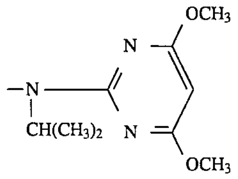 | 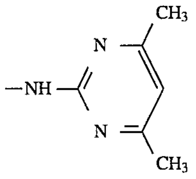 | 178 |
| 176 | O | 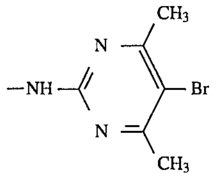 | 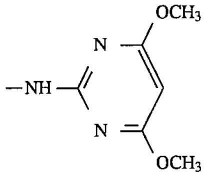 | 212 |

TABLE 2-continued
Examples of the compounds of the formula (I)
| Ex. No. | Q | R¹ | R² | Melting point (°C.) |
|---|---|---|---|---|
| 177 | O | 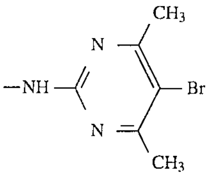 | 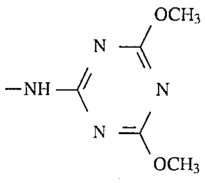 | 216 |
| 178 | O | 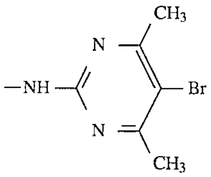 | 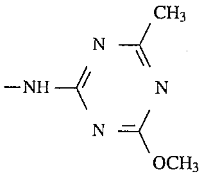 | 228 |
| 179 | O | 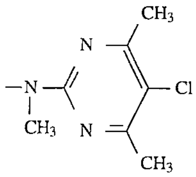 | 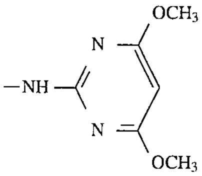 | 198 |
| 180 | O | 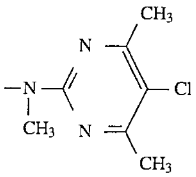 | 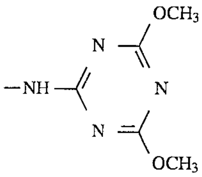 | 196 |
| 181 | O | 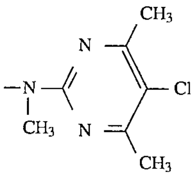 | 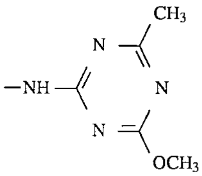 | 161 |
| 182 | O | 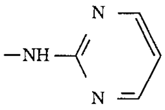 | 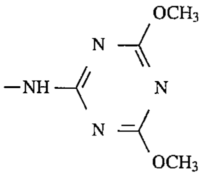 | 204 |
| 183 | O | 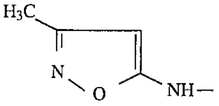 | 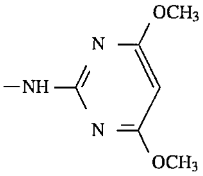 | 105 |
| 184 | O | 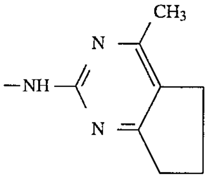 | 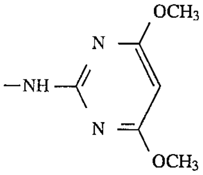 | 201 |

TABLE 2-continued
Examples of the compounds of the formula (I)
| Ex. No. | Q | $R^1$ | $R^2$ | Melting point (°C.) |
|---|---|---|---|---|
| 185 | O | 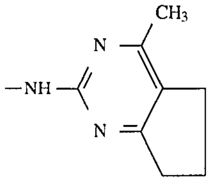 | 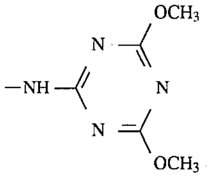 | 198 |
| 186 | O | 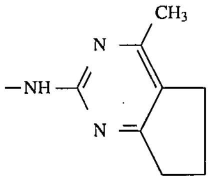 | 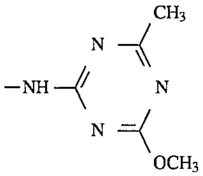 | 198 |
| 187 | O | 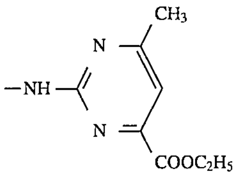 | 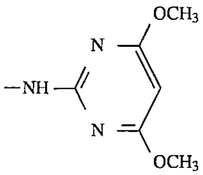 | 174 |
| 188 | O | 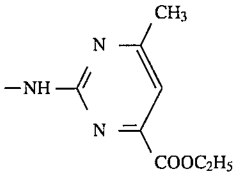 | 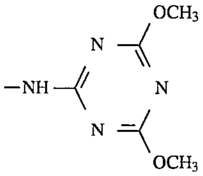 | 108 |
| 189 | O | 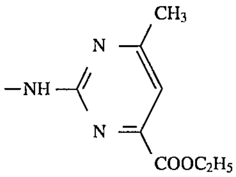 | 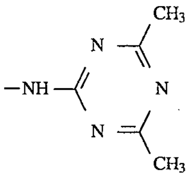 | 165 |
| 190 | O | 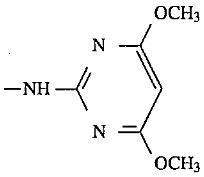 | 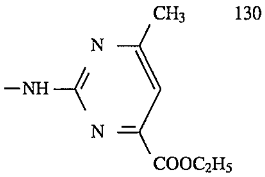 | 130 |
| 191 | O | 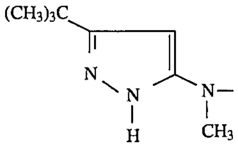 | 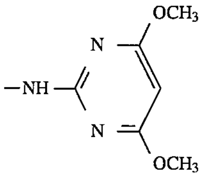 | |
| 192 | O | 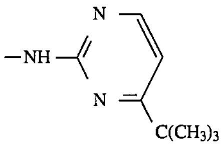 | 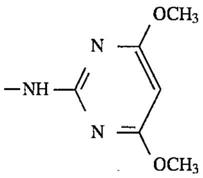 | |

TABLE 2-continued
Examples of the compounds of the formula (I)
| Ex. No. | Q | $R^1$ | $R^2$ | Melting point (°C.) |
|---|---|---|---|---|
| 193 | O | 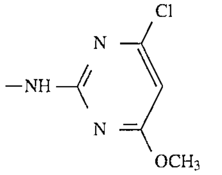 | 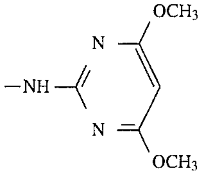 | |
| 194 | O | 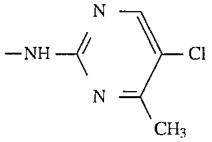 | 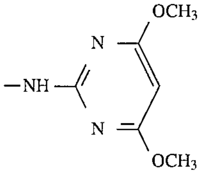 | |
| 195 | O | 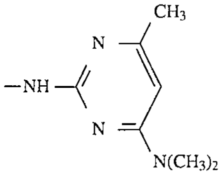 | 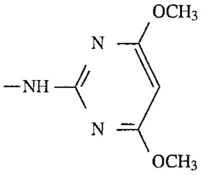 | |
| 196 | O | 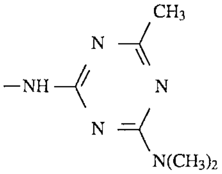 | 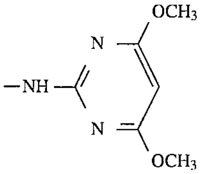 | |
| 197 | O | 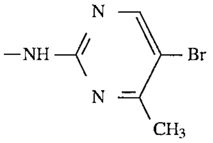 | 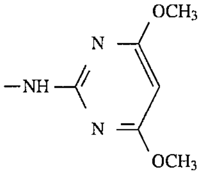 | |
| 198 | O | 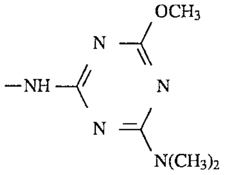 | 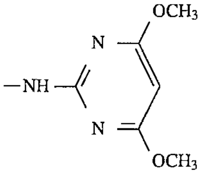 | |
| 199 | O | 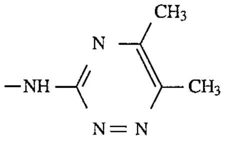 | 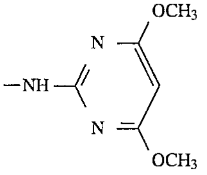 | |
| 200 | O | 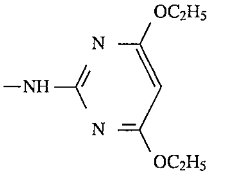 | 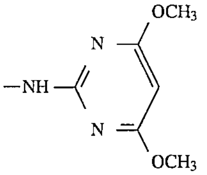 | |

TABLE 2-continued
Examples of the compounds of the formula (I)
| Ex. No. | Q | $R^1$ | $R^2$ | Melting point (°C.) |
|---|---|---|---|---|
| 201 | O | 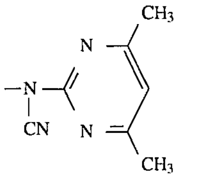 | 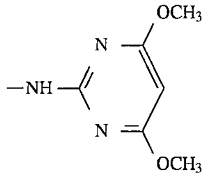 | |
| 202 | O | 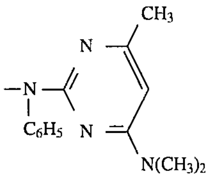 | 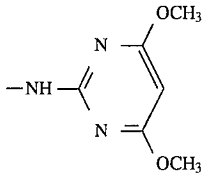 | |
| 203 | O | 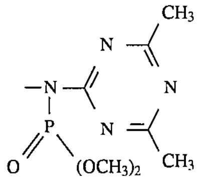 | 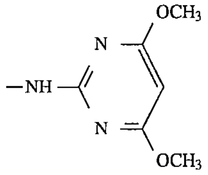 | |
| 204 | O | 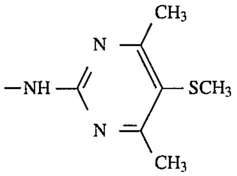 | 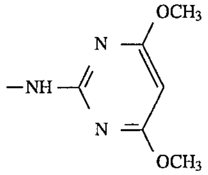 | |
| 205 | O | 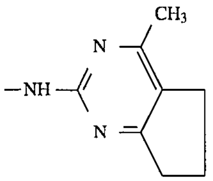 | 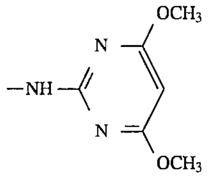 | |
| 206 | O | 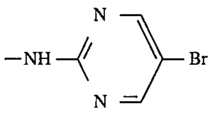 | 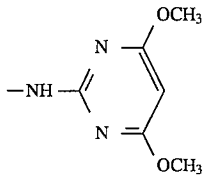 | |
| 207 | O | 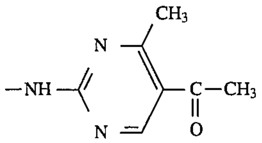 | 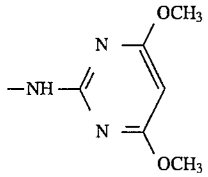 | |
| 208 | O | 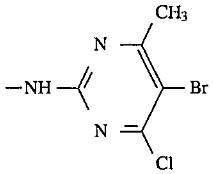 | 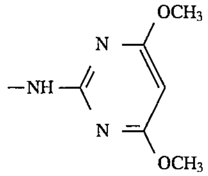 | |

TABLE 2-continued
Examples of the compounds of the formula (I)
| Ex. No. | Q | $R^1$ | $R^2$ | Melting point (°C.) |
|---|---|---|---|---|
| 209 | O | 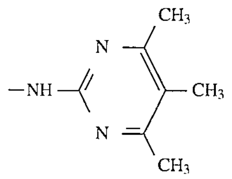 | 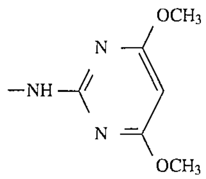 | |
| 210 | O | 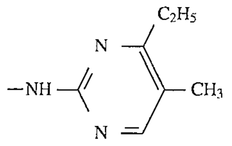 | 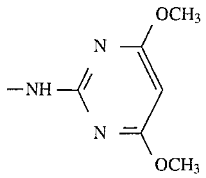 | |
| 211 | O | 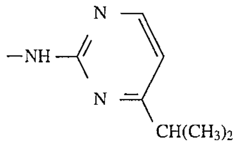 | 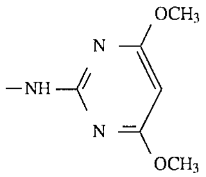 | |
| 212 | O | 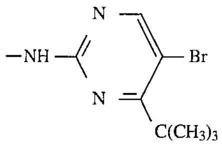 | 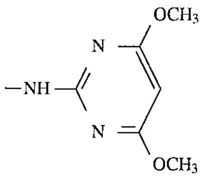 | |
| 213 | O | 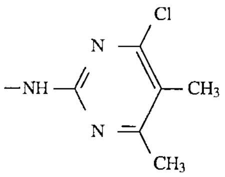 | 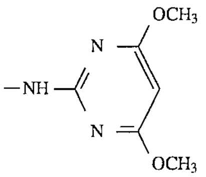 | |
| 214 | O | 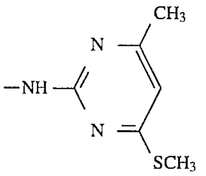 | 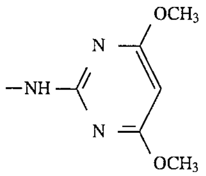 | |
| 215 | O | 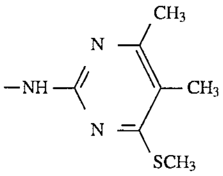 | 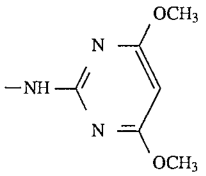 | |
| 216 | O | 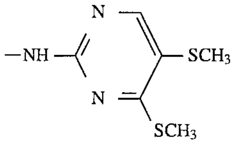 | 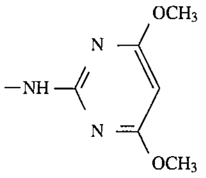 | |

TABLE 2-continued
Examples of the compounds of the formula (I)
| Ex. No. | Q | $R^1$ | $R^2$ | Melting point (°C.) |
|---|---|---|---|---|
| 217 | O | 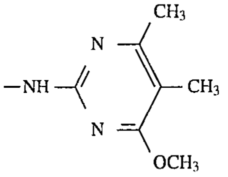 | 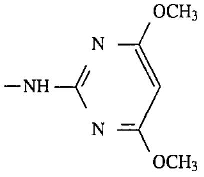 | |
| 218 | O | 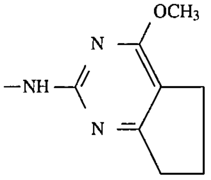 | 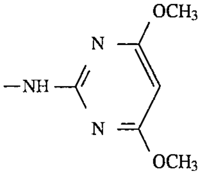 | |
| 219 | O | 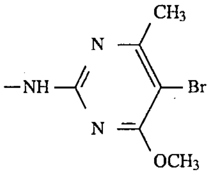 | 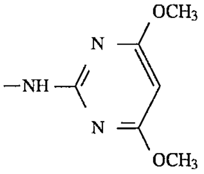 | |
| 220 | O | 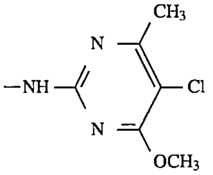 | 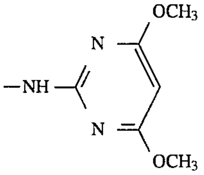 | |
| 221 | O | 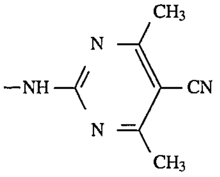 | 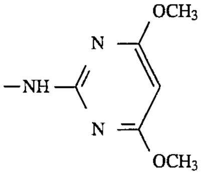 | |
| 222 | O | 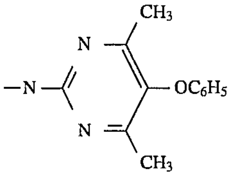 | 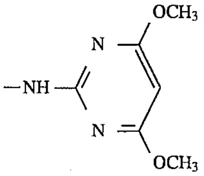 | |
| 223 | O | 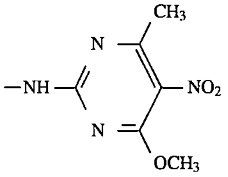 | 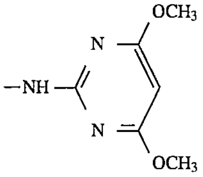 | |
| 224 | O | 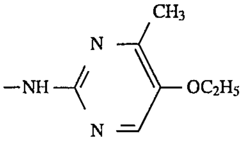 | 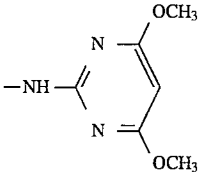 | |

TABLE 2-continued

Examples of the compounds of the formula (I)

| Ex. No. | Q | $R^1$ | $R^2$ | Melting point (°C.) |
|---|---|---|---|---|
| 225 | O | 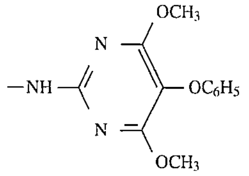 | 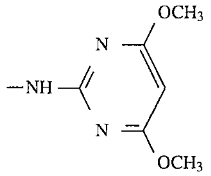 | |
| 226 | O | 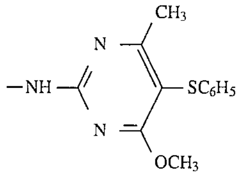 | 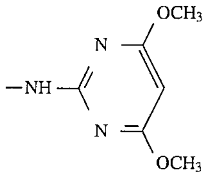 | |
| 227 | O | 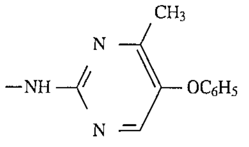 | 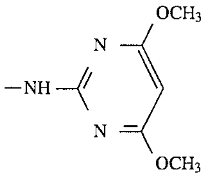 | |
| 228 | O | 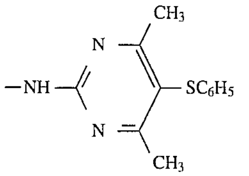 | 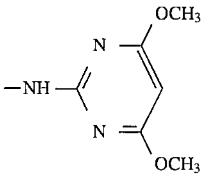 | |
| 229 | O | 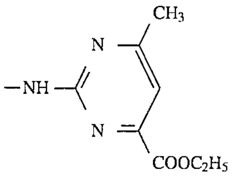 | 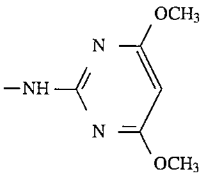 | (amorphous)*) |

*)obtained in the form of the sodium salt

Note:

The examples of Tables 1 and 2 can also be used to illustrate the above definition of $R^1/R^2$—"a radical from the series comprising heterocyclyl, heterocyclylamino and heterocyclylimino, bonded via N":

a) heterocyclic radicals which contain at least 1 nitrogen atom in the ring skeleton can be bonded to the central sulphonylamino(thio)carbonyl unit (—$SO_2$—NH—CQ—) either via such a ring nitrogen atom or via an amino or imino nitrogen atom as connecting member;

b) however, heterocyclic radicals which do not contain a nitrogen atom in the ring skeleton must always be bonded to the central sulphonylamino(thio)carbonyl unit via an amino or imino nitrogen atom as connecting member;

c) a more exact term for "heterocyclylimino" would be "heterocyclylideneimino"; this is to be understood as meaning heterocyclic radicals having an exocyclic C═N double bond (compare, for example, $R^1$ in Examples 54, 55 and 65) which are bonded to the central sulphonylamino (thio)carbonyl unit via precisely this imino nitrogen atom.

Example A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. After three weeks, the degree of damage to the plants is rated in % damage in comparison to the development of the untreated control.

The figures denote:

0%=no action (like untreated control)

100%=total destruction

In this test, a powerful activity against weeds combined with a good tolerance by wheat and barley is shown, for example, by the compound of Preparation Example 3. The same applies analogously to the compounds of Preparation Examples 19, 92, 93, 96, 101, 102, 103, 150 and 153.

TABLE A

Post-emergence test/greenhouse

| Active compound | (Example No.: cf. Table 2) | Application rate (g/ha) | Barley | Wheat | Datura | Galinsoga | Helianthus | Ipomoea | Sinapis |
|---|---|---|---|---|---|---|---|---|---|
| 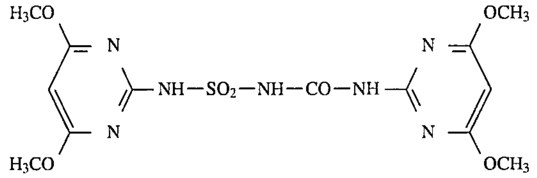 | | | | | | | | | |
| | (3) | 60 | 0 | 0 | 90 | 90 | 100 | 95 | 100 |
| | (19) | 125 | 10 | 0 | 90 | 80 | 100 | 70 | 95 |
| | (92) | 250 | 0 | 0 | 70 | 90 | 95 | 90 | 100 |
| | (93) | 250 | 0 | 0 | 80 | 95 | 100 | 70 | 100 |
| | (96) | 250 | 0 | 0 | 100 | 30 | 100 | 80 | 100 |
| | (101) | 250 | 0 | 0 | 100 | 95 | 100 | 90 | 100 |
| | (102) | 250 | 0 | 0 | 95 | 95 | 100 | 90 | 100 |
| | (103) | 250 | 0 | 0 | 100 | 100 | 100 | 90 | 100 |
| | (150) | 250 | 0 | 0 | 90 | 70 | 100 | 70 | 100 |
| | (153) | 250 | 0 | 0 | 100 | 95 | 100 | 95 | 100 |

Example B

Pre-emergence test

Solvent: 5 parts by weight of acetone

Emulsifier: I part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test too, the compounds according to the invention exhibit a very powerful activity against weeds.

We claim:

1. Heterocyclically disubstituted sulphonylaminocarbonyl compounds of the general formula (I)

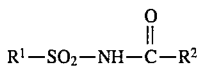

(I)

in which $R^1$ represents an optionally substituted radical selected from the group consisting of

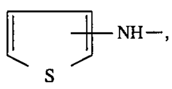

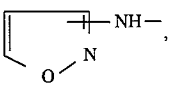

-continued

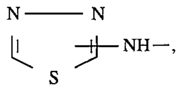

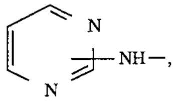

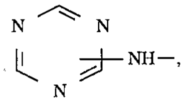

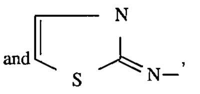

and $R^2$ represents the 2,4-dihydro-3H-1,2,4-triazol-3-on-2-yl radical of the formula

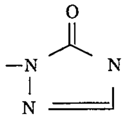

which is optionally substituted in its 4-position, its 5-position, or both, and wherein the substituents for $R^1$ and $R^2$ are selected from the group consisting of fluorine, chlorine, bromine, iodine, cyano, nitro, carboxyl, carbamoyl, amino, hydroxyl, formyl; $C_1$–$C_5$-alkyl, $C_5$–$C_6$-alkanediyl, $C_2$–$C_5$-alkenyl, $C_2$–$C_5$-alkinyl, $C_3$–$C_6$-cycloalkyl, $C_3$–$C_6$-cycloalkyl-$C_1$–$C_3$-alkyl, $C_1$–$C_5$-alkoxy, $C_2$–$C_5$-alkenyloxy, $C_2$–$C_5$-alkinyloxy, $C_1$–$C_5$-alkylthio, $C_2$–$C_5$-alkenylthio, $C_2$–$C_5$-alkinylthio, $C_1$–$C_5$-alkylsulphinyl, $C_1$–$C_5$-alkylsulphonyl, $C_1$–$C_5$-alkylamino, di-($C_1$–$C_3$-alkyl)-amino, $C_1$–$C_5$-alkyl-carbonyl, $C_3$–$C_6$-cycloalkyl-carbonyl, $C_1$–$C_5$-alkoxy-carbonyl, $C_1$–$C_2$-alkoxy-$C_1$–$C_2$-alkoxy-carbonyl, di-($C_1$–$C_3$-alkyl)-amino-carbonyl, dimethoxyphosphoryl, diethoxyphosphoryl, dimethoxythiophosphoryl and diethoxythiophosphoryl, each of which is optionally substituted by fluorine or chlorine; phenyl, phenoxy, phenylthio, phenylsulphinyl, phenylsulphonyl, phenyl-$C_1$–$C_3$-alkyl and phenyl-$C_2$–$C_3$-alkenyl, each of which is optionally substituted by fluorine, chlorine, bromine, iodine, cyano, nitro, carboxyl, carbamoyl, amino, hydroxyl, formyl, $C_1$–$C_4$-alkyl (which is optionally substituted by fluorine or chlorine), $C_1$–$C_4$-alkoxy (which is optionally substituted by fluorine or chlorine), $C_1$–$C_4$-alkylthio, $C_1$–$C_4$-alkylsulphinyl, $C_1$–$C_4$-alkylsulphonyl (each of which is optionally substituted by fluorine and/or chlorine) and $C_1$–$C_4$-alkoxycarbonyl, and salts of the compounds of the formula (I).

2. The compound of claim 1, wherein $R^1$ represents pyrimidine-2-yl-amino or 1,3,5-triazine-2-yl-amino, both of which can be substituted by fluorine, chlorine, bromine, methyl, ethyl, propyl, isopropyl, cyclopropyl, methoxy, ethoxy, propoxy, isopropoxy, chloromethyl, dichloromethyl, trichloromethyl, fluoromethyl, difluoromethyl, trifluoromethyl, methoxymethyl, ethoxymethyl, methoxyethyl, ethoxyethyl, difluoromethoxy, chloroethoxy, dichloroethoxy, trichloroethoxy, fluoroethoxy, difluoroethoxy, trifluoroethoxy, methylthio, ethylthio, methylamino, ethylamino or dimethylamino, and wherein the amino group which links the heterocycle is optionally methylated; and $R^2$ represent 2,4-dihydro-3H-1,2,4-triazole-3-on-2-yl which is optionally substituted by fluorine, chlorine, bromine, methyl, ethyl, propyl, isopropyl, butyl, isobutyl, sec-butyl, fluoromethyl, difluoromethyl, trifluoromethyl, chloromethyl, dichloromethyl, trichloromethyl, fluoroethyl, difluoroethyl, trifluoroethyl, chloroethyl, dichloroethyl, trichloroethyl, chlorodifluoromethyl, fluorodichloromethyl, chlorodifluoroethyl, trifluorochloroethyl, methoxy, ethoxy, propoxy, isopropoxy, butoxy, isobutoxy, sec-butoxy, methylthio, ethylthio, propylthio, isopropylthio, butylthio, isobutylthio, sec-butylthio, amino, methylamino, ethylamino, propylamino, isopropylamino, butylamino, isobutylamino, sec-butylamino, dimethylamino, diethylamino, cyclopropyl, cyclobutyl, cyclopentyl or cyclohexyl.

3. A herbicidal composition, comprising a herbicidally effective amount of at least one compound according to claim 1.

4. Method of combating weeds which comprises contacting said weeds with a herbicidally effective amount of a compound according to claim 1.

* * * * *